United States Patent
Hoflack et al.

(10) Patent No.: US 10,676,486 B2
(45) Date of Patent: Jun. 9, 2020

(54) MACROCYCLIC RIP2 KINASE INHIBITORS

(71) Applicant: ONCODESIGN S.A., Dijon (FR)

(72) Inventors: Jan Hoflack, Westmalle (BE); Petra Blom, Destelbergen (BE); Pascal Benderitter, St. Apollinaire (FR)

(73) Assignee: ONCODESIGN S.A., Dijon (FR)

( * ) Notice: Subject to any disclaimer, the term of this patent is extended or adjusted under 35 U.S.C. 154(b) by 443 days.

(21) Appl. No.: 15/505,976

(22) PCT Filed: Sep. 17, 2015

(86) PCT No.: PCT/EP2015/071347
§ 371 (c)(1),
(2) Date: Feb. 23, 2017

(87) PCT Pub. No.: WO2016/042087
PCT Pub. Date: Mar. 24, 2016

(65) Prior Publication Data
US 2019/0127390 A1    May 2, 2019

(30) Foreign Application Priority Data

Sep. 17, 2014  (EP) .................................. 14185130

(51) Int. Cl.
*C07D 487/00* (2006.01)
*C07D 498/22* (2006.01)
*A61P 29/00* (2006.01)

(52) U.S. Cl.
CPC ............ *C07D 498/22* (2013.01); *A61P 29/00* (2018.01)

(58) Field of Classification Search
CPC ............................... C07D 498/22; A61P 29/00
USPC ....................................................... 540/471
See application file for complete search history.

(56) References Cited

U.S. PATENT DOCUMENTS

| | | | |
|---|---|---|---|
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |

FOREIGN PATENT DOCUMENTS

| EP | 0721331 B1 | 12/2001 |
|---|---|---|
| WO | WO2008058126 A2 | 5/2008 |
| WO | WO2011146336 A1 | 11/2011 |
| WO | WO2013001310 A1 | 1/2013 |
| WO | WO2013025958 A1 | 2/2013 |
| WO | WO2013045653 A1 | 4/2013 |
| WO | WO2013046029 A1 | 4/2013 |

OTHER PUBLICATIONS

International Search Report and Written Opinion, completed Oct. 23, 2015, pertaining to PCT/EP2015/071347 filed Sep. 17, 2015.
International Preliminary Report on Patentability, completed Aug. 25, 2016, pertaining to PCT/EP2015/071347, filed Sep. 17, 2015.
Chin et al., "Rip2: A Key Molecule that Regulates both Innate and Acquired Immunity", Curr. Med. Chem (2005) 4, pp. 35-42.
Becker et al., "Blau Syndrome and Related Genetic Disorders Causing Childhood Arthritis", Current Rheumatology Reports (2005) 7, pp. 427-433.
Tigno-Aranjeuz et al., "Inhibition of RIP2's tyrosine kinase activity limits NOD2-driven cytokine responses", Genes & Development 24:2666 (2010) 1, pp. 2666-2677.
Girardin et al., "CARD4/Nod1 mediates NF-KB and JNK activation by invasive Shigella flexneri", EMBO reports (2001) vol. 2, No. 8, pp. 736-742.
Hysi et al., "NOD1 variation, immunoglobulin E and asthma", Human Molecular Genetics (2005), vol. 14, No. 7, pp. 935-941.
McGovern et al., "Association between a complex insertion/deletion polymorphism in NOD1 (CARD4) and susceptibility to inflammatory bowel disease", Human Molecular Genetics (2005), vol. 14, No. 10, pp. 1245-1250.
Wiken et al., "Higher Monocyte Expressioin of TLR2 and TLR4, and Enhanced Pro-inflammatory Synergy of TLR2 with NOD2 Stimulation in Sarcoidosis", Journal of Clinical Immunology (2009) 29, pp. 78-89.
Inohara et al., "An Induced Proximity Model for NF-KB Activation in the Nod1/RICK and RIP Signaling Pathways", The Journal of Biological Chemistry, (2000), vol. 275, No. 36, pp. 27823-27831.
Hollenbach et al., "Inhibition of RICK/Nuclear Factor-KB and p38 Signaling Attenuates the Inflammatory Response in a Murine Model of Crohn Disease", The Journal of Biological Chemistry (2005), vol. 280, No. 15, pp. 14981-14988.
Lesage et al., "CARD15/NOD2 Mutational Analysis and Genotype-Phenotype Correlation in 612 Patients with Inflammatory Bowel Disease", Am . J. Hum. Genet. (2002), 70, pp. 845-857.
Strober et al., "Signalling pathways and molecular interactions of NOD1 and NOD2", Nature Reviews Immunology (2006) 6, pp. 9-20.
Brooks et al., "Erlotinib and Gefitinib, Epidermal Growth Factor REceptor Kinase Inhibitors, May Treat Non-Cancer-Related Tumor Necrosis Factor-a Mediated Inflammatory Diseases", (2013) 18, pp. e-3-e-5.
Yamamoto et al., "Role of Nod2 in the development of Crohn's disease", (2009) 11, pp. 912-918.
Jehara et al., "PR3-ANCA in Wegener's granulomatosis prime human mononuclear cells for enhanced activation via TLRs and NOD 1/2", Diagnostic Pathology, (2009), 4:23.
Nature Genetics "CARD15 mutations in Blau syndrome", (2001), 29, pp. 19-20.

*Primary Examiner* — Taylor V Oh
(74) *Attorney, Agent, or Firm* — Dinsmore & Shohl, LLP

(57) ABSTRACT

The present invention relates to macrocyclic compounds and compositions containing said compounds acting as kinase inhibitors, in particular as inhibitors of RIP2 and/or mutants thereof, for use in the diagnosis, prevention and/or treatment of RIP2-kinase associated diseases. Moreover, the present invention provides methods of using said compounds, for instance as a medicine or diagnostic agent.

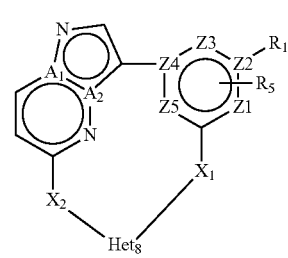

9 Claims, No Drawings

MACROCYCLIC RIP2 KINASE INHIBITORS

FIELD OF THE INVENTION

The present invention relates to macrocyclic compounds and compositions containing said compounds acting as kinase inhibitors, in particular as inhibitors of RIP2, and/or mutants thereof, for use in the diagnosis, prevention and/or treatment of RIP2-kinase associated diseases. Moreover, the present invention provides methods of using said compounds, for instance as a medicine or diagnostic agent.

BACKGROUND OF THE INVENTION

Protein kinases constitute a large family of structurally related enzymes that are responsible for the control of a wide variety of signal transduction processes in the cell. They have been shown to be key regulators in most cellular functions including proliferation, cell metabolism, cell survival, apoptosis, DNA damage repair, cell motility . . . . Uncontrolled signalling due to defective control of protein phosphorylation has been implicated in a number of diseases, including, for example, cancer, inflammation, allergies, immune diseases, CNS disorders, angiogenesis . . . .

Amongst the families of protein kinases, one particular example is the Receptor-Interacting Serine/Threonine Kinases including RIP2. RIP2 (Receptor-Interacting Protein 2) is also referred to as Card-Containing Ice-Associated Kinase (CARDIAK), CARD3 (C-terminal CAspase-Recruitment Domain 3), Receptor-Interacting Protein Kinase 2 (RIPK2), or Rip-Like Interacting Clarp Kinase (RICK). RIP2 kinase is composed of an N-terminal kinase domain and a C-terminal caspase-recruitment domain (CARD) linked via an intermediate (IM) region (Curr. Med. Chem. (2005) 4, 35-42)). The CARD domain of RIP2 kinase mediates interaction with other CARD-containing proteins, such as the Nucleotide Oligomerization Domain Proteins, NOD1 and NOD2 (J. Biol. Chem. (2000) 275, 27823-27831 and EMBO reports (2001) 2, 736-742). NOD1 and NOD2 are cytoplasmic receptors which are activated by specific bacterial peptidoglycan motifs and play a key role in innate immune surveillance. Upon intracellular bacterial exposure, NOD1 or NOD2 binds to the protein kinase RIP2 to coordinate NF-κB (nuclear factor κ B)-mediated cytokine responses. Once associated with NOD1/2, RIP2 undergoes autophosphorylation on Tyr 474 (Y474), and acts as a molecular scaffold to bring together other kinases (TAK1, IKKα/β/γ) involved in NF-κB and MAPK activation (Nature Reviews Immunology (2006) 6, 9-20).

Both NOD1/2 and RIP2 are NF-κB regulated genes, and as such, their activation causes a positive feedback loop in which activation of NOD1/2:RIP2 stimulates further activation and further inflammation. Additionally, NOD1/2 and RIP2 expression are stimulated by a variety of mediators of inflammation, including TNF (Tumor Necrosis Factor) and IFN (Interferon). In addition to NF-κB pathway activation, the NOD1/2:RIP2 complex stimulates autophagy, bacteriocidal activity, MHC Class II presentation and MAPK (Mitogen-Activated Protein Kinase) activation. Overall, this pathway modulates the innate immune system to help tailor the adaptive immune response to eradicate the offending pathogen.

Dysregulation of RIP2-dependent signaling has been linked to autoinflammatory diseases. Patients with loss-of-function NOD2 alleles are prone to the development of Crohn's disease, an inflammatory disorder of the gastrointestinal tract (Am. J. Hum. Genet. (2002) 70, 845-857 and Microbes and Infection (2009) 11, 912-918). In contrast, gain-of-function NOD2 mutations have been genetically linked to other inflammatory diseases, such as Blau Syndrome/Early Onset Sarcoidosis (EOS), a pediatric granulomateous disease characterized by uveitis, dermatitis, and arthritis (Nature Genetics (2001) 29, 19-20 and Current Rheumatology Reports (2005) 7, 427-433). Mutations in NOD1 have been associated with asthma (Hum. Mol. Genet. (2005) 14, 935-941), and early-onset and extra-intestinal inflammatory bowel disease (Hum. Mol. Genet. (2005) 14, 1245-1250). Genetic and functional studies have also suggested a role for RIP2-dependent signaling in a variety of other granulomateous disorders, such as sarcoidosis (Journal of Clinical Immunology (2009) 29, 78-89) and Wegner's Granulomatosis (Diagnostic Pathology (2009) 4, 23).

The fact that both loss-of-function polymorphisms and gain-of-function mutations cause inflammatory diseases is likely due to the fact that NOD2 functions as a rheostat to help maintain normal immunologic homeostasis. Lack of coordination between inflammatory signaling pathways influences the development of inflammatory disorders, and the NOD1/2:RIP2 activation equilibrium is central to this coordination. Treatments for Crohn's disease and sarcoidosis currently rely on broad, non-specific immunologic inhibition (e.g., corticosteroids) or on specific cytokine inhibition (e.g., anti-TNF therapies) with significant costs and side effects. Treatment is less than ideal, however, because not all agents are equally efficacious, the diseases occur over long time frames, and not all agents remain efficacious in the same patient. The RIP2 Y474 autophosphorylation event has been shown to be necessary for effective NOD2 signaling and does not occur in the presence of the most common loss-of-function Crohn's disease-associated NOD2 allele. This autophosphorylation is inhibited by non highly selective kinase inhibitors, Gefitinib and Erlotinib, suggesting that RIP2's tyrosine kinase activity could be targeted specifically in the treatment of inflammatory diseases (Genes Dev. (2010) 1, 2666-77). Several clinical cases were reported about Gefitinib or Erlotinib treatment being efficient to clear psoriasis or reduce arthritic symptoms or insulin-resistant type 2 diabetes associated with metabolic syndrome (The Oncologist (2013) 18: e3-e5). In mouse established models of chronic inflammatory bowel diseases, inhibition of RIP2 activity by the small molecule SB203580 is efficacious to reduce induced-colitis (J Biol Chem. (2005) 15, 14981-14988.). None of these small molecules however, primarily and selectively targets RIP2. It was therefore an object of the present invention to provide a potent, selective, small molecule inhibitor of RIP2 kinase activity which can block specifically RIP2-dependent pro-inflammatory signaling and thereby provides a therapeutic benefit in autoinflammatory diseases characterized in increased and/or dysregulated RIP2 kinase activity.

We have now found that the macrocyclic pyrazolopyrimidines and imidazopyridazines and pharmaceutically acceptable compositions according to this invention are useful for the treatment of inflammatory disorders, in particular Crohn's disease, bowel disease, Sarcoidosis, psoriasis, rheumatoid arthritis, asthma and insulin-resistant type 2 diabetes, ulcerative colitis, lupus, uveitis, blau syndrome, granulomatous inflammation, in particular behget's disease, multiple sclerosis, and diseases associated with RIP2 kinase activity (i.e. RIP2-kinase associated diseases).

SUMMARY OF THE INVENTION

We have surprisingly found that the macrocyclic compounds described herein act as RIP2 kinase inhibitors, and are thus very useful in the diagnosis, prevention and/or treatment of RIP2-kinase associated diseases.

In a first objective the present invention provides a compound of Formula I or a stereoisomer, tautomer, racemic, metabolite, pro- or pre-drug, salt, hydrate, N-oxide form, or solvate thereof,

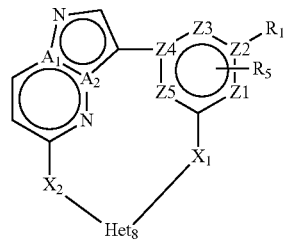

I

Wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl; wherein when $A_2$ is N, then $R_1$ and $R_5$ are not simultaneously —H;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_1$ $Z_1$, $Z_2$, $Z_3$, $Z_4$ and $Z_5$ are each independently selected from C and N; and $A_1$ and $A_2$ are each independently selected from C and N.

In a particular embodiment, the present invention provides a compound of Formula I or a stereoisomer, tautomer, racemic, metabolite, pro- or pre-drug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —O—$C_{1-6}$alkyl, and —S—$C_{1-6}$alkyl; wherein when $A_2$ is N, then $R_1$ and $R_5$ are not simultaneously —H;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, and —$NR_3$—;

$X_2$ is selected from —O—$CH_2$—, —S—$CH_2$—, and —$NR_2$—$CH_2$—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_1$ $Z_1$, $Z_2$, $Z_3$, $Z_4$ and $Z_5$ are each independently selected from C and N; and $A_1$ and $A_2$ are each independently selected from C and N.

In a particular embodiment, the present invention provides a compound of Formula I or a stereoisomer, tautomer, racemic, metabolite, pro- or pre-drug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$; —O—$C_{1-6}$alkyl, and —S—$C_{1-6}$alkyl; wherein when $A_2$ is N, then $R_1$ and $R_5$ are not simultaneously —H.

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —S—$C_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a bivalent 3- to 10-membered heterocycle having from 1 to 3 heteroatoms selected from O, N and S;

wherein at least one of said heteroatoms is attached to X$_1$; and wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N; and A$_1$ and A$_2$ are each independently selected from C and N.

In a particular embodiment, the present invention provides a compound of Formula Ia or a stereoisomer, tautomer, racemic, metabolite, pro- or pre-drug, salt, hydrate, N-oxide form, or solvate thereof,

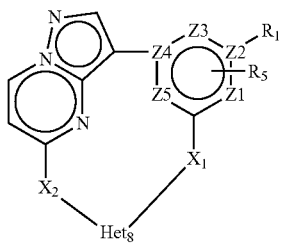

Ia

Wherein

R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{29}$, R$_{30}$, R$_{31}$, R$_{32}$, R$_{33}$, R$_{34}$, R$_{37}$ and R$_{38}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{35}$R$_{36}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;

wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

wherein when R$_1$ is —H, then at least one heteroatom of Het$_8$ is attached to X$_1$ Z$_1$, Z$_2$, Z$_3$, Z$_4$ and Z$_5$ are each independently selected from C and N.

In a particular embodiment, the present invention provides a compound of Formula Ia or a stereoisomer, tautomer, racemic, metabolite, pro- or pre-drug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -Het;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, and —$NR_3$—;

$X_2$ is selected from —O—$CH_2$—, —S—$CH_2$—, and —$NR_2$—$CH_2$—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
  wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;
  wherein when $R_1$ is —H, then at least one heteroatom of $Het_8$ is attached to $X_1$ $Z_1$, $Z_2$, $Z_3$, $Z_4$ and $Z_5$ are each independently selected from C and N.

In a particular embodiment, the present invention provides a compound of Formula Ia or a stereoisomer, tautomer, racemic, metabolite, pro- or pre-drug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{29}$, $R_{30}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_6$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_6$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a bivalent 3- to 10-membered heterocycle having from 1 to 3 heteroatoms selected from O, N and S; wherein at least one of said heteroatoms is attached to X$_1$; and wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

In a particular embodiment, the present invention provides a compound of Formula Ia or a stereoisomer, tautomer, racemic, metabolite, pro- or pre-drug, salt, hydrate, N-oxide form, or solvate thereof, wherein

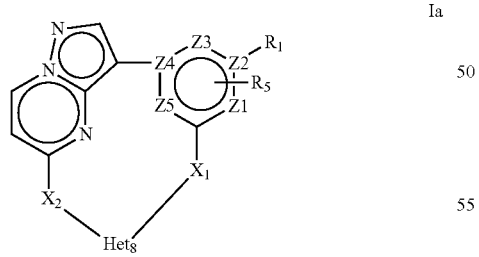

Ia

R$_1$ is selected from -halo, —C$_{1-6}$alkyl and —CN;
R$_5$ is attached to Z$_1$ and is selected from —H, -halo, —C$_{1-6}$alkyl, and —C$_{3-6}$cycloalkyl;
R$_2$ is selected from —H, —C$_{1-6}$alkyl and —C$_{3-6}$cycloalkyl;
X$_1$ is selected from —O—C$_{1-6}$alkyl, and —NR$_3$—C$_{1-6}$alkyl-;
X$_2$ is —NR$_2$—C$_{1-6}$alkyl;
Het$_8$ is a 3- to 10-membered N-containing heterocycle; and
Z$_1$, Z$_2$, Z$_3$, Z$_4$ and Z$_5$ are each C.

In a specific embodiment the present invention provides a compound selected from the list comprising:

Compound O1, Example O1

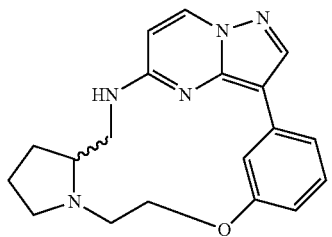

Compound O2, Example O2

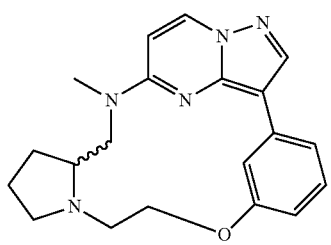

Compound O3, Example O3

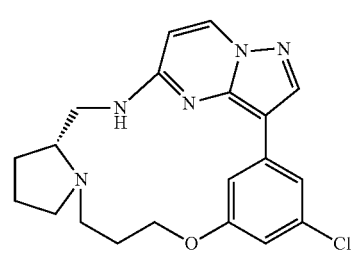

Compound O4, Example O4

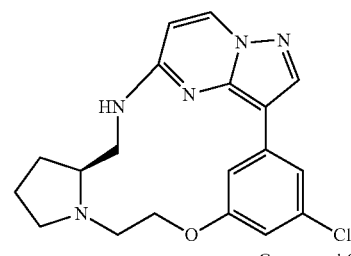

Compound O5, Example O5

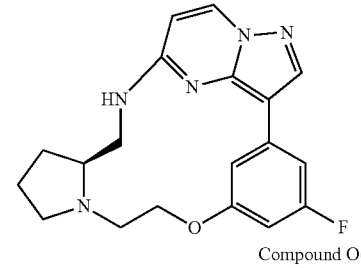

Compound O6, Example O6

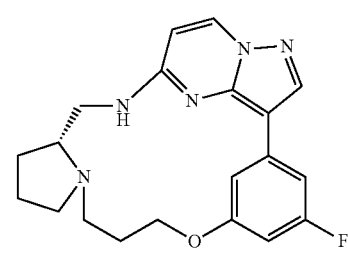

-continued

Compound O7, Example O7

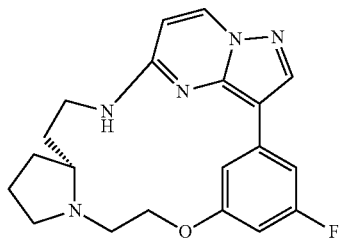

Compound O8, Example O8

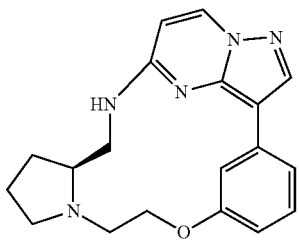

Compound O9, Example O9

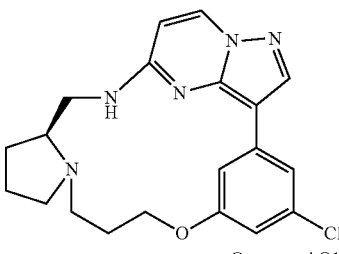

Compound O10, Example O10

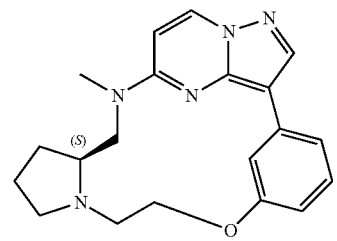

Compound O11, Example O11

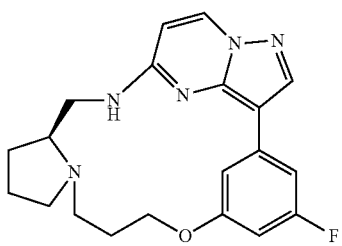

Compound O12, Example O12

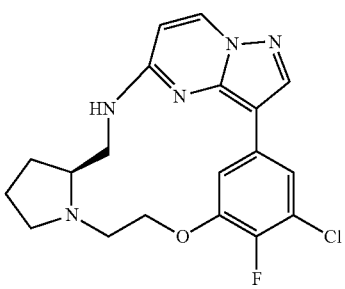

-continued

Compound O13, Example O13

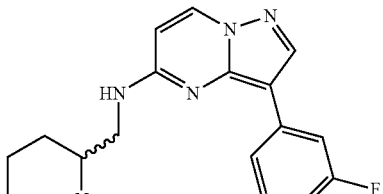

Compound O14, Example O14

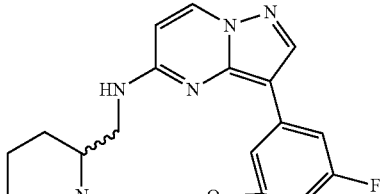

In yet a further aspect, the present invention provides a compound according to the present invention; wherein $R_5$ is linked to the aryl or heteroaryl moiety at position $Z_1$ in accordance with the numbering as provided in Formula I or Ia.

In yet a further aspect, the present invention provides a compound according to the present invention; wherein said compound is the S-enantiomer.

The present invention further provides a pharmaceutical composition comprising a compound according to this invention.

In a further aspect, the present invention provides a compound or a composition according to this invention, for use as a medicine.

In a particular embodiment, the present invention provides a compound or composition according to this invention for use in the diagnosis, prevention and/or treatment of a RIP2-kinase associated disease. Said RIP2-kinase associated disease may in particular be an inflammatory disorders, more in particular selected from the list comprising: Crohn's disease, bowel disease, Sarcoidosis, psoriasis, rheumatoid arthritis, asthma, ulcerative colitis, lupus, uveitis, blau syndrome, granulomatous inflammation, in particular behget's disease, multiple sclerosis and insulin-resistant type 2 diabetes.

Furthermore, the present invention provides the use of a compound or composition according to this invention, suitable for inhibiting the activity of a kinase; in particular a RIP2 kinase; or for the diagnosis, prevention and/or treatment of a RIP2-kinase associated disease.

Finally, the present invention provides a method for prevention and/or treatment of a RIP2-kinase associated disease; said method comprising administering to a subject in need thereof a compound or a composition according to the present invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides a compound of Formula I or a stereoisomer, tautomer, racemic, metabolite, pro- or pre-drug, salt, hydrate, N-oxide form, or solvate thereof,

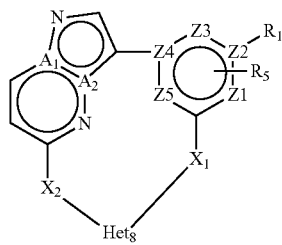

I

Wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_8$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl; wherein when $A_2$ is N, then $R_1$ and $R_5$ are not simultaneously —H;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$;

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_1$ $Z_1$, $Z_2$, $Z_3$, $Z_4$ and $Z_5$ are each independently selected from C and N; and $A_1$ and $A_2$ are each independently selected from C and N.

Unless indicated otherwise, all of the above radicals can be read both ways. For example, when $X_1$ is —$NR_3$—$C_{1-6}$alkyl-, the —$C_{1-6}$alkyl- may be attached to $Het_8$ and —$NR_3$— attached to the $Z_1$-$Z_5$ aryl or heteroaryl moiety. Alternatively, the —$C_{1-6}$alkyl- may be attached to the $Z_1$-$Z_5$ aryl or heteroaryl moiety and —$NR_3$— attached to $Het_8$. What is called "left part" of a radical is for example when $X_1$ is —$NR_3$—$C_{1-6}$alkyl-, —$NR_3$—, and the "right part" is —$C_{1-6}$alkyl-.

Preferably, $X_1$ is such as the left part of the possible values of $X_1$ (i.e. in particular —O from —O—$C_{1-6}$alkyl, —S from —S—$C_{1-6}$alkyl, —$NR_3$ from —$NR_3$—$C_{1-6}$alkyl, etc) is attached to the $Z_1$-$Z_5$ aryl or heteroaryl moiety. Alternatively, $X_1$ is such as the right part of the possible values of $X_1$ (i.e. in particular ($C_{1-6}$alkyl)- from —O—$C_{1-6}$alkyl, —S—$C_{1-6}$alkyl and —$NR_3$—$C_{1-6}$alkyl, etc) is attached to the $Z_1$-$Z_5$ aryl or heteroaryl moiety.

Preferably, $X_2$ is such as the left part of the possible values of $X_2$ (i.e. in particular —O from —O—$C_{1-6}$alkyl, —S from —S—$C_{1-6}$alkyl, —$NR_2$ from —$NR_2$—$C_{1-6}$alkyl, etc) is attached to the pyrazolopyrimidine moiety. Alternatively, $X_2$ is such as the right part of the possible values of $X_2$ (i.e. in particular ($C_{1-6}$alkyl)- from —O—$C_{1-6}$alkyl, —S—$C_{1-6}$alkyl and —$NR_2$—$C_{1-6}$alkyl, etc) is attached to the pyrazolopyrimidine moiety.

The same principle applies to all the radicals of the invention unless specified otherwise.

When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopropyl, cyclobutyl, cyclopentyl, and cyclohexyl.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -halo, —OH, primary and secondary amides, —O—$C_{1-6}$alkyl, —S—$C_{1-6}$alkyl, heteroaryl, aryl, and the like.

The term "cycloalkyl" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a $C_3$ alkylene group may be for example *—$CH_2CH_2CH_2$—*, *—CH(—$CH_2CH_3$)—*, or *—$CH_2$CH(—$CH_3$)—*. Likewise a $C_3$ cycloalkylene group may be

The terms "heterocycle" as used herein by itself or as part of another group refer to non-aromatic, fully saturated or partially unsaturated cyclic groups (for example, 3 to 6 membered monocyclic ring systems, or 8-10 membered bicyclic rings) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrahydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, tetrahydrofuranyl,

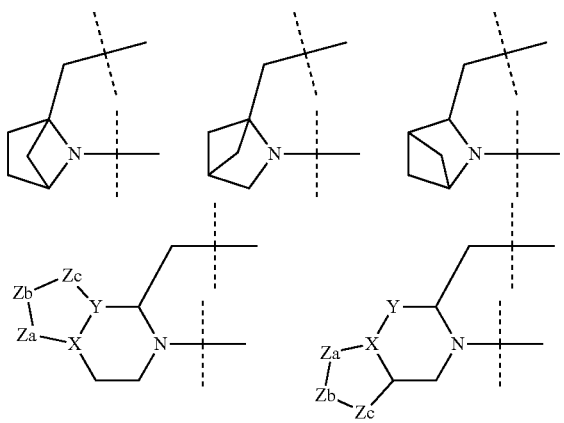

-continued

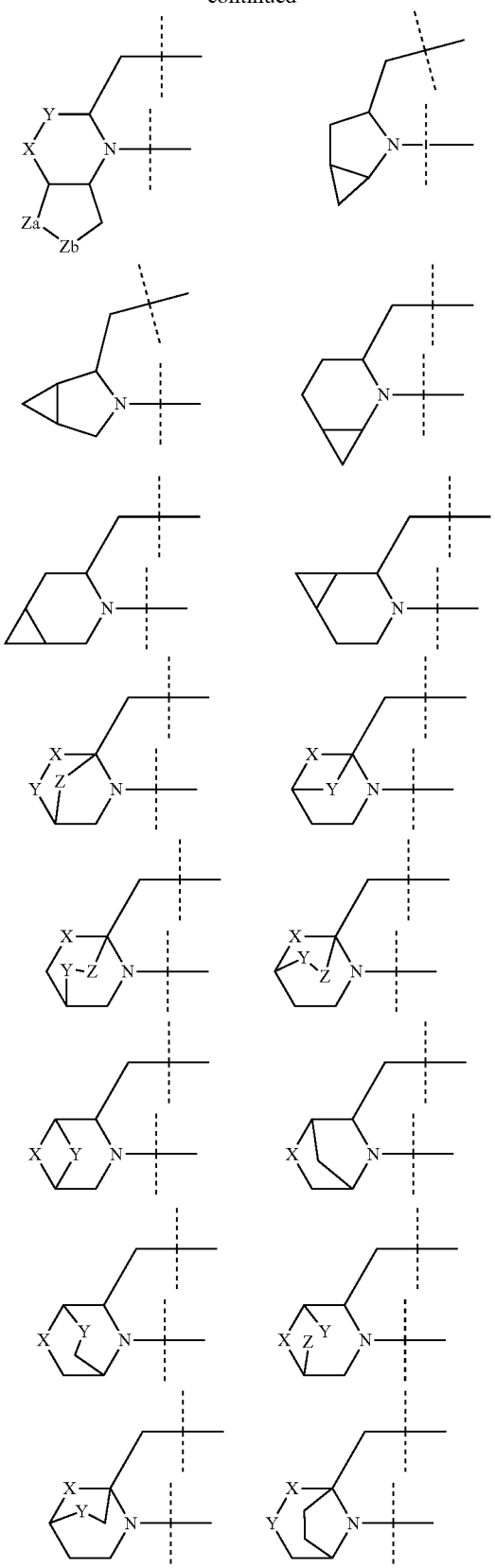

wherein X, Y, Z, Za, Zb and Zc represent a C atom or suitable heteroatom, selected from N, O and S.

8-10 Membered heterocyclic groups are also meant to include spiro-groups, which are bicyclic compounds with both rings connected through a single atom, such as for example spiro[4.5]decane, which is a spiro compound consisting of a cyclohexane ring and a cyclopentane ring, further suitable 8-10 membered heterocyclic groups are represented herein below:

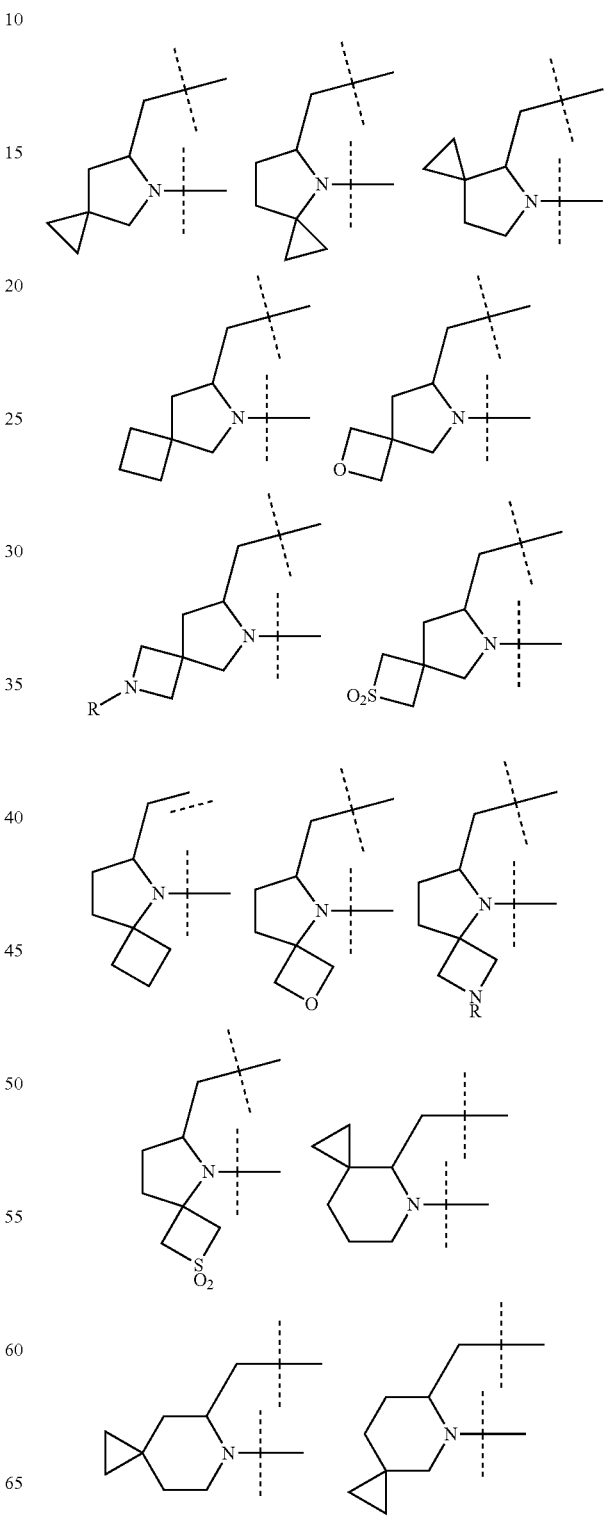

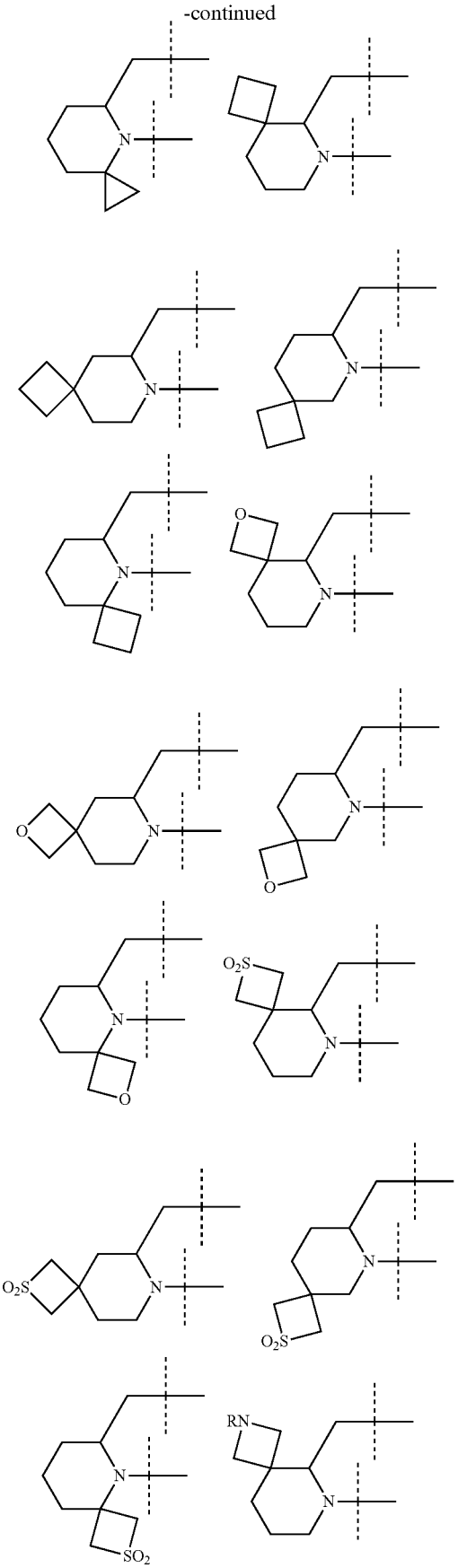

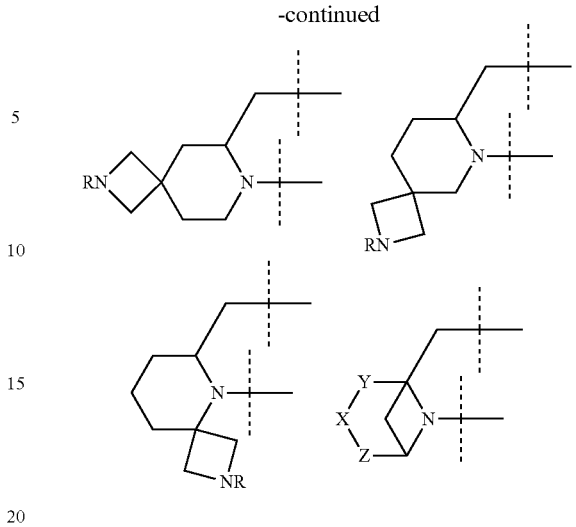

wherein R represents a substituent selected from the list as defined for any one of Het₁ to Het₇.

The term "aryl" as used herein refers to a polyunsaturated, aromatic hydrocarbyl group having from 5-10 atoms. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 10 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3- benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent.

Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as $^3$H, $^{11}$C, $^{13}$N, $^{14}$C, $^{15}$O and $^{18}$F. Such isotopically-labelled compounds of formula (I) are useful in drug and/or substrate tissue distribution assays. For example $^{11}$C and $^{18}$F isotopes are particularly useful in PET (Positron Emission Tomography). PET is useful as a diagnostic or treatment follow-up tool that can be applied in a translational manner in a preclinical and clinical setting. It also has applications in PK determination of compounds, including biodistribution. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

Preferably, compounds of Formula I are defined as such that $A_1$ and $A_2$ are selected from C and N; wherein when $A_1$ is C, then $A_2$ is N; and wherein when $A_2$ is C, then $A_1$ is N; provided that when $A_2$ is N, then $R_1$ and $R_5$ are not simultaneously —H.

More preferably, $A_1$ is N and $A_2$ is C. Alternatively, $A_2$ is N and $A_1$ is C; provided that when $A_2$ is N, then $R_1$ and $R_5$ are not simultaneously —H.

Preferably, $R_1$ is selected from —H, halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl.

More preferably, $R_1$ is selected from —F, —Cl, —CN, —O—$C_{1-6}$alkyl, —O—$C_{1-6}$cycloalkyl; wherein each of said —$C_{1-6}$alkyl is optionally and independently substituted with from 1 to 3 -Me, -halo, —OH, —H, —cyclopropyl, -cyclobutyl; -cycloalkyls are optionally independently substituted by -Me, -halo, —OH, —H.

Preferably, $R_5$ is attached to $Z_1$ or $Z_5$ and is selected from —H, halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —$NR_6$—$SO_2$—$R_8$, —$C_{3-6}$cycloalkyl, —O—$C_{3-6}$cycloalkyl, —$Ar_5$ and $Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl.

More preferably, $R_5$ is selected from —F, —Cl, —CN, —$C_{1-3}$alkyl, —$C_{3-4}$cycloalkyl; wherein each of said —$C_{1-3}$alkyl is optionally and independently substituted with from 1 to 3 -Me, -halo, —OH, —H; wherein each of said —$C_{3-4}$cycloalkyl is optionally and independently substituted with from 1 to 3 -Me, -halo, —OH, —H.

Preferably, $R_2$ is selected from —H, -halo, —OH, —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$.

More preferably, $R_2$ is selected from —H, —$C_{1-3}$alkyl, —$C_{3-4}$cycloalkyl; wherein each of said —$C_{1-3}$alkyl is optionally and independently substituted with from 1 to 3 -H, -Me, -halo, —OH, —$NR_{13}R_{14}$. wherein each of said —$C_{3-4}$cycloalkyl is optionally and independently substituted with from 1 to 3 —H, -Me, -halo, —OH, —$NR_{13}R_{14}$.

Preferably, $R_3$ is selected from —H, -halo, —OH, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$.

More preferably, $R_3$ is selected from $C_{1-3}$alkyl, $C_{3-4}$cycloalkyl; wherein each of said —$C_{1-3}$alkyl is optionally and independently substituted with from 1 to 3 —H, -Me, -halo, —OH, —$NR_{15}R_{16}$. wherein each of said —$C_{3-4}$cycloalkyl is optionally and independently substituted with from 1 to 3 —H, -Me, -halo, —OH, —$NR_{15}R_{16}$.

Preferably, $R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$.

More preferably, $R_4$ is selected from —$C_{1-3}$alkyl, —O—$C_{1-3}$alkyl, —$NR_{17}R_{18}$, —$C_{3-4}$cycloalkyl, —O—$C_{3-4}$cycloalkyl; wherein each of said $C_{1-3}$alkyl is optionally and independently substituted with from 1 to 3 —H, -Me, -halo, —OH, —$NR_{17}R_{18}$. wherein each of said —$C_{3-4}$cycloalkyl is optionally and independently substituted with from 1 to 3 —H, -Me, -halo, —OH, —$NR_{17}R_{18}$.

More preferably, $R_8$ is selected from —$C_{1-3}$alkyl, —O—$C_{1-3}$alkyl, —$NR_{17}R_{18}$, —$C_{3-4}$cycloalkyl, —O—$C_{3-4}$cycloalkyl; wherein each of said —$C_{1-3}$alkyl is optionally and independently substituted with from 1 to 3 —H, -Me, -halo, —OH, —$NR_{17}R_{18}$. wherein each of said —$C_{3-4}$cycloalkyl is optionally and independently substituted with from 1 to 3 —H, -Me, -halo, —OH, —$NR_{17}R_{18}$.

Preferably, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$.

Preferably, $R_{27}$ and $R_{28}$, are each independently selected from —H, —$C_{1-6}$alkyl, —$C_{3-6}$cycloalkyl and -$Het_2$.

More preferably, $R_{27}$ and $R_{28}$, are each independently selected from —H, —$C_{1-3}$alkyl, —$C_{3-4}$cycloalkyl; wherein each of said —$C_{1-3}$alkyl is optionally and independently substituted with from 1 to 3 —H, -Me, -halo; and wherein each of said —$C_{3-4}$cycloalkyl is optionally and independently substituted with from 1 to 3 —H, -Me, -halo.

Preferably, $R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$.

More preferably, $R_{37}$ and $R_{38}$, are each independently selected from —H, —$C_{1-3}$alkyl, or —$C_{3-4}$cycloalkyl; wherein each of said —$C_{1-3}$alkyl is optionally and independently substituted with from 1 to 3 —H, -Me, -halo; and wherein each of said —$C_{3-4}$cycloalkyl is optionally and independently substituted with from 1 to 3 —H, -Me, -halo, —OH.

Preferably, $X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$.

More preferably, $X_1$ is selected from —O—$C_{1-3}$alkyl, —$NR_3$—$C_{1-3}$alkyl-; wherein each of said —$C_{1-3}$alkyl is optionally and independently substituted with from 1 to 3 -H, -halo, —$CF_3$, —$CHF_2$, —$C_{1-3}$alkyl, —C or substituted to form a cyclopropyl, cyclobutyl or oxetane; wherein each of said cyclopropyl, cyclobutyl or oxetane is optionally and independently substituted with from 1 to 3 —H, -Me, -halo, —OH Preferably, $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$.

More preferably, $X_2$ is selected from —O—$C_1$alkyl-, —$NR_2$—$C_1$alkyl; wherein each of said —$C_1$alkyl is optionally and independently substituted with from 1 to 2 —H, -halo, -Me or bi-substituted to form a cyclopropyl, cyclobutyl, oxetane; wherein each of said cyclopropyl, cyclobutyl or oxetane is optionally and independently substituted with from 1 to 3 —H, -Me, -halo, —OH Preferably, $Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, —$NR_{13}R_{20}$; wherein each of said —$C_{1-6}$alkyl is optionally and independently substituted with from 1 to 3 -halo.

More preferably, $Ar_1$, $Ar_4$, $Ar_5$, $Ar_6$, and $Ar_7$ are each independently selected from any 5 or 6 membered aromatic ring.

Preferably, $Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo.

More preferably, $Het_1$, $Het_2$, $Het_4$, $Het_5$, $Het_6$, and $Het_7$ are each independently selected from any 5 or 6 membered saturated or unsaturated heterocycle.

Preferably, $Het_8$ is a 3- to 10-membered heterocycle having from 1 to 3 heteroatoms selected from O, N and S;
wherein said $Het_8$ is optionally and independently substituted with from 1 to 6 substituents selected from —H, -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;
wherein when $R_1$ is —H, then at least one heteroatom of $Het_8$ is attached to $X_1$ More preferably, $Het_8$ is selected from pyrrolidine or piperidine, and optionally and independently substituted with from 1 to 6 substituents selected from —H, -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo.

Preferably, $Z_1$, $Z_2$, $Z_3$, $Z_4$ and $Z_5$ are each independently selected from C and N.

More preferably, $Z_1$, $Z_2$, $Z_3$, $Z_4$ and $Z_5$ are each C.

In a particular embodiment, the present invention provides a compound of Formula I or a stereoisomer, tautomer, racemic, metabolite, pro- or pre-drug, salt, hydrate, N-oxide form, or solvate thereof; wherein one or more of the following applies:
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl; wherein when $A_2$ is N, then $R_1$ and $R_5$ are not simultaneously —H;

R₅ is attached to Z₁ or Z₅ and is selected from —H, -halo, —OH, —C₁₋₆alkyl, —O—C₁₋₆alkyl, —S—C₁₋₆alkyl, —NR₆R₇, —(C═O)—R₈, —(C═S)—R₈, —SO₂—R₈, —CN, —NR₆—SO₂—R₈, —C₃₋₆cycloalkyl, —O—C₃₋₆cycloalkyl, —Ar₅ and -Het₅; wherein each of said —C₁₋₆alkyl is optionally and independently substituted with from 1 to 3 substituents selected from -halo, —OR₃₆, —NR₂₃R₂₄, —O—C₁₋₆alkyl, and —S—C₁₋₆alkyl;

R₂ is selected from —H, -halo, —OH, —C₁₋₆alkyl, and —C₃₋₆cycloalkyl; wherein each of said —C₁₋₆alkyl is optionally and independently substituted with from 1 to 3 substituents selected from -halo, —OR₂₇, and —NR₁₃R₁₄;

R₃ is selected from —H, -halo, —OH, —C₁₋₆alkyl, —C₃₋₆cycloalkyl; wherein each of said —C₁₋₆alkyl is optionally and independently substituted with from 1 to 3 substituents selected from -halo, —OR₂₈, and —NR₁₅R₁₆;

R₄ and R₈ are each independently selected from -halo, —OH, —C₁₋₆alkyl, —O—C₁₋₆alkyl, —S—C₁₋₆alkyl, —NR₁₇R₁₈, —C₃₋₆cycloalkyl, —O—C₃₋₆cycloalkyl, —Ar₄ and -Het₄;

R₆, R₇, R₉, R₁₀, R₁₁, R₁₂, R₁₃, R₁₄, R₁₅, R₁₆, R₁₇, R₁₈, R₁₉, R₂₀, R₂₁, R₂₂, R₂₃, R₂₄, R₃₁, R₃₂, R₃₃, R₃₄, R₃₅ and R₃₆ are each independently selected from —H, -halo, ═O, —OH, —C₁₋₆alkyl, —O—C₁₋₆alkyl, —S—C₁₋₆alkyl, —C₃₋₆cycloalkyl, —Ar₆ and -Het₆; wherein each of said —C₁₋₆alkyl is optionally and independently substituted with from 1 to 3 substituents selected from -halo, —OH, —O—C₁₋₆alkyl, —S—C₁₋₆alkyl, —C₃₋₆cycloalkyl, -Het₆, —Ar₆ and —NR₃₇R₃₈;

R₂₇ and R₂₈, are each independently selected from —H, —C₁₋₆alkyl, —C₃₋₆cycloalkyl and -Het₂:

R₃₇ and R₃₈, are each independently selected from —H, -halo, —OH, —C₁₋₆alkyl, —O—C₁₋₆alkyl, —S—C₁₋₆alkyl, —C₃₋₆cycloalkyl, —Ar₇ and -Het₇;

X₁ is selected from —C₁₋₆alkyl-, —O—C₁₋₆alkyl-, —S—C₁₋₆alkyl-, —C₁₋₆alkyl-NR₃—C₁₋₆alkyl-, —NR₃—C₁₋₆alkyl-, —NR₃—, and —O—; wherein each of said —C₁₋₆alkyl- is optionally and independently substituted with from 1 to 3 substituents selected from -halo, —OH, —C₁₋₆alkyl, —O—C₁₋₆alkyl, —S—C₁₋₆alkyl, -phenyl, and —NR₃₃R₃₄;

X₂ is selected from —C₁₋₆alkyl-, —O—C₁₋₆alkyl-, —S—C₁₋₆alkyl-, —C₁₋₆alkyl-NR₂—C₁₋₆alkyl-, —NR₂—C₁₋₆alkyl-, —NR₂—, and —O—; wherein each of said —C₁₋₆alkyl- is optionally and independently substituted with from 1 to 3 substituents selected from -halo, —OH, —C₁₋₆alkyl, —O—C₁₋₆alkyl, —S—C₁₋₆alkyl, -phenyl and —NR₃₁R₃₂;

Ar₁, Ar₄, Ar₅, Ar₆, and Ar₇ are each independently a 5- to 10-membered aromatic cycle optionally comprising 1 to 3 heteroatoms selected from O, N and S; each of said Ar₁, Ar₄, Ar₅, Ar₆, and Ar₇ being optionally and independently substituted with from 1 to 3 substituents selected from -halo, —OH, —C₁₋₆alkyl, —O—C₁₋₆alkyl, —S—C₁₋₆alkyl, and —NR₁₉R₂₀; wherein each of said —C₁₋₆alkyl is optionally and independently substituted with from 1 to 3 -halo;

Het₁, Het₂, Het₄, Het₅, Het₆, and Het₇ are each independently a 3- to 10-membered heterocycle having from 1 to 3 heteroatoms selected from O, N and S; wherein each of said Het₁, Het₂, Het₄, Het₅, Het₆, and Het₇ is optionally and independently substituted with from 1 to 3 substituents selected from -halo, —OH, —C₁₋₆alkyl, —O—C₁₋₆alkyl, —S—C₁₋₆alkyl, ═O, —(C═O)—C₁₋₆alkyl, and —NR₂₁R₂₂; wherein each of said —C₁₋₆alkyl is optionally and independently substituted with from 1 to 3 -halo;

Het₈ is a 3- to 10-membered heterocycle having from 1 to 3 heteroatoms selected from O, N and S;
wherein said Het₈ is optionally and independently substituted with from 1 to 3 substituents selected from -halo, —OH, —C₁₋₆alkyl, —O—C₁₋₆alkyl, —S—C₁₋₆alkyl, ═O, —(C═O)—C₁₋₆alkyl, and —NR₂₁R₂₂; wherein each of said —C₁₋₆alkyl is optionally and independently substituted with from 1 to 3 -halo;
wherein when R₁ is —H, then at least one heteroatom of Het₈ is attached to X₁

Z₁, Z₂, Z₃, Z₄ and Z₅ are each independently selected from C and N; and

A₁ and A₂ are each independently selected from C and N.

In a further embodiment, the present invention provides a compound of Formula I or a stereoisomer, tautomer, racemic, metabolite, pro- or pre-drug, salt, hydrate, N-oxide form, or solvate thereof,

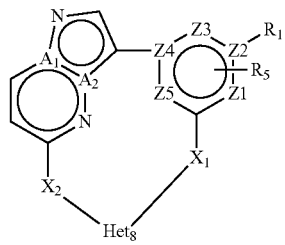

Wherein

R₁ is selected from —H, -halo, —OH, —C₁₋₆alkyl, —O—C₁₋₆alkyl, —S—C₁₋₆alkyl, —NR₉R₁₀, —(C═O)—R₄, —(C═S)—R₄, —SO₂—R₄, —CN, —NR₉—SO₂—R₄, —C₃₋₆cycloalkyl, —O—C₃₋₆cycloalkyl, —Ar₁ and -Het₁; wherein each of said —C₁₋₆alkyl is optionally and independently substituted with from 1 to 3 substituents selected from -halo, —OR₃₅, —NR₁₁R₁₂, —O—C₁₋₆alkyl, and —S—C₁₋₆alkyl;

R₅ is attached to Z₁ or Z₅ and is selected from —H, -halo, —OH, —C₁₋₆alkyl, —O—C₁₋₆alkyl, —S—C₁₋₆alkyl, —NR₆R₇, —(C═O)—R₈, —(C═S)—R₈, —SO₂—R₈, —CN, —NR₆—SO₂—R₈, —C₃₋₆cycloalkyl, —O—C₃₋₆cycloalkyl, —Ar₅ and -Het₅; wherein each of said —C₁₋₆alkyl is optionally and independently substituted with from 1 to 3 substituents selected from -halo, —OR₃₆, —NR₂₃R₂₄, —O—C₁₋₆alkyl, and —S—C₁₋₆alkyl;

R₂ is selected from —H, -halo, —OH, —C₁₋₆alkyl, and —C₃₋₆cycloalkyl; wherein each of said —C₁₋₆alkyl is optionally and independently substituted with from 1 to 3 substituents selected from -halo, —OR₂₇, and —NR₁₃R₁₄;

R₃ is selected from —H, -halo, —OH, —C₁₋₆alkyl, —C₃₋₆cycloalkyl; wherein each of said —C₁₋₆alkyl is optionally and independently substituted with from 1 to 3 substituents selected from -halo, —OR₂₈, and —NR₁₅R₁₆;

R₄ and R₈ are each independently selected from -halo, —OH, —C₁₋₆alkyl, —O—C₁₋₆alkyl, —S—C₁₋₆alkyl, —NR₁₇R₁₈, —C₃₋₆cycloalkyl, —O—C₃₋₆cycloalkyl, —Ar₄ and -Het₄;

R₆, R₇, R₉, R₁₀, R₁₁, R₁₂, R₁₃, R₁₄, R₁₅, R₁₆, R₁₇, R₁₈, R₁₉, R₂₀, R₂₁, R₂₂, R₂₃, R₂₄, R₃₁, R₃₂, R₃₃, R₃₄, R₃₅ and R₃₆ are each independently selected from —H, -halo, ═O, —OH, —C₁₋₆alkyl, —O—C₁₋₆alkyl, —S—C₁₋₆alkyl, —C₃₋₆cycloalkyl, —Ar₆ and -Het₆; wherein each of said —C₁₋₆alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
  wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;
  wherein when $R_1$ is —H, then at least one heteroatom of $Het_8$ is attached to $X_1$ $Z_1$, $Z_2$, $Z_3$, $Z_4$ and $Z_5$ are each independently selected from C and N; and $A_1$ and $A_2$ are each independently selected from C and N provided that said compound is not

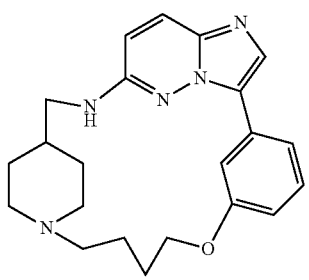 [SMILES: c1cc2cc(c1)-c1cnc3ccc(nn13)NCC1CCN(CCCCO2)CC1]

In particular, $X_1$, and $X_2$ as used herein, represent biradicals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Referring to formula I:

$X_1$ is selected from the list comprising *—$C_{1-6}$alkyl-, *—O—$C_{1-6}$alkyl-, *—S—$C_{1-6}$alkyl-, *—$C_{1-6}$alkyl-$NR_3$—$C_{1-6}$alkyl-, *—$NR_3$—$C_{1-6}$alkyl-, *—$NR_3$—, *—O—; * wherein said biradical is preferably attached to the aryl or heteroaryl moiety via *;

$X_2$ is selected from the list comprising *—$C_{1-6}$alkyl-, *—$C_{1-6}$alkyl-$NR_2$—$C_{1-6}$alkyl-, *—$NR_2$—$C_{1-6}$alkyl-, *—$NR_2$—, *—O—; * wherein said biradical is preferably attached to the pyrazolopyrimidine moiety via *;

In yet a further embodiment, the present invention provides a compound of Formula I or a stereoisomer, tautomer, racemic, metabolite, pro- or pre-drug, salt, hydrate, N-oxide form, or solvate thereof; wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$; —O—$C_{1-6}$alkyl, and —S—$C_{1-6}$alkyl; wherein when $A_2$ is N, then $R_1$ and $R_5$ are not simultaneously —H;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -Het; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, and —$NR_3$—;

$X_2$ is selected from —O—$CH_2$—, —S—$CH_2$—, and —$NR_2$—$CH_2$—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
  wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;
  wherein when $R_1$ is —H, then at least one heteroatom of $Het_8$ is attached to $X_1$ $Z_1$, $Z_2$, $Z_3$, $Z_4$ and $Z_5$ are each independently selected from C and N; and $A_1$ and $A_2$ are each independently selected from C and N.

In another embodiment, the present invention provides a compound of Formula I or a stereoisomer, tautomer, racemic, metabolite, pro- or pre-drug, salt, hydrate, N-oxide form, or solvate thereof; wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —O—$C_{1-6}$alkyl, and —S—$C_{1-6}$alkyl; wherein when $A_2$ is N, then $R_1$ and $R_5$ are not simultaneously —H.

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_6$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_6$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S;

wherein at least one of said heteroatoms is attached to $X_1$; and wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

In a further particular embodiment, the present invention provides a compound of Formula Ia or a stereoisomer, tautomer, racemic, metabolite, pro- or pre-drug, salt, hydrate, N-oxide form, or solvate thereof; wherein

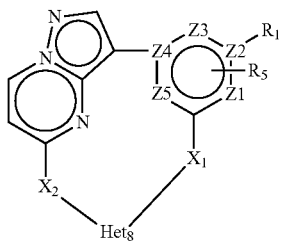

Ia

Wherein
R₁ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;
R₅ is attached to Z₁ or Z₅ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;
R₂ is selected from —H, -halo, —OH, —C$_{1-6}$alkyl, —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;
R₃ is selected from —H, -halo, —OH, —C$_{1-6}$alkyl, —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;
R₄ and R₈ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;
R₆, R₇, R₈, R₉, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{27}$, R$_{28}$, R$_{29}$, R$_{30}$, R$_{31}$, R$_{32}$, R$_{33}$, R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{35}$R$_{36}$;
R$_{27}$ and R$_{28}$, are each independently selected from —H, —C$_{1-6}$alkyl, —C$_{3-6}$cycloalkyl and Het$_2$:
R$_{35}$ and R$_{36}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;
X₁ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$
X₂ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;
Ar₁, Ar₄, Ar₅, Ar₆, and Ar₇ are each independently a 5- to 10-membered aromatic cycle optionally comprising 1 to 3 heteroatoms selected from O, N and S; each of said Ar₁, Ar₄, Ar₅, Ar₆, and Ar₇ being optionally and independently substituted with from 1 to 3 substituents selected from -halo, —OH, —C$_{1-6}$alkyl, —O—C$_{1-6}$alkyl, —S—C$_{1-6}$alkyl, —NR$_{19}$R$_{20}$; wherein each of said —C$_{1-6}$alkyl is optionally and independently substituted with from 1 to 3 -halo;
Het₁, Het₂, Het₄, Het₅, Het₆, and Het₇ are each independently a 3- to 10-membered heterocycle having from 1 to 3 heteroatoms selected from O, N and S; wherein each of said Het₁, Het₂, Het₄, Het₅, Het₆, and Het₇ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;
Het₈ is a 3- to 10-membered heterocycle having from 1 to 3 heteroatoms selected from O, N and S;
wherein said Het₈ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;
wherein when R₁ is —H, then at least one heteroatom of Het₈ is attached to X₁
Z₁, Z₂, Z₃, Z₄ and Z₅ are each independently selected from C and N.
Preferably, compounds of Formula Ia are defined as such that
Preferably, R₁ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_5$, —CN, —NR$_9$—SO$_2$—R$_4$, —C$_{3-6}$cycloalkyl, —O—C$_{3-6}$cycloalkyl, —Ar$_1$ and —Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl.
More preferably, R₁ is selected from —F, —Cl, —CN, —O—C$_{1-6}$alkyl, —O—C$_{1-6}$cycloalkyl; wherein each of said —C$_{1-6}$alkyl is optionally and independently substituted with from 1 to 3 -Me, -halo, —OH, —H, cyclopropyl, cyclobutyl; cycloalkyls are optionally independently substituted by -Me, -halo, —OH, —H.
Preferably, R₅ is attached to Z₁ or Z₅ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$ cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl.
More preferably, R₅ is selected from —F, —Cl, —CN, —C$_{1-3}$alkyl, —C$_{3-4}$cycloalkyl; wherein each of said —C$_{1-3}$alkyl is optionally and independently substituted with from 1 to 3 -Me, -halo, —OH, —H; wherein each of said C$_{3-4}$cycloalkyl is optionally and independently substituted with from 1 to 3 -Me, -halo, —OH, —H.
Preferably, R₂ is selected from —H, -halo, —OH, —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$.

More preferably, $R_2$ is selected from —H, —$C_{1-3}$alkyl, —$C_{3-4}$cycloalkyl; wherein each of said —$C_{1-3}$alkyl is optionally and independently substituted with from 1 to 3 —H, -Me, -halo, —OH, —$NR_{13}R_{14}$. wherein each of said $C_{3-4}$cycloalkyl is optionally and independently substituted with from 1 to 3 —H, -Me, -halo, —OH, —$NR_{13}R_{14}$.

Preferably, $R_3$ is selected from —H, -halo, —OH, $C_{1-6}$alkyl, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$.

More preferably, $R_3$ is selected from $C_{1-3}$alkyl, $C_{3-4}$cycloalkyl; wherein each of said —$C_{1-3}$alkyl is optionally and independently substituted with from 1 to 3 —H, -Me, -halo, —OH, —$NR_{15}R_{16}$. wherein each of said —$C_{3-4}$cycloalkyl is optionally and independently substituted with from 1 to 3 —H, -Me, -halo, —OH, —$NR_{15}R_{16}$.

Preferably, $R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$.

More preferably, $R_4$ is selected from —$C_{1-3}$alkyl, —O—$C_{1-3}$alkyl, —$NR_{17}R_{18}$, —$C_{3-4}$cycloalkyl, —O—$C_{3-4}$cycloalkyl; wherein each of said —$C_{1-3}$alkyl is optionally and independently substituted with from 1 to 3 —H, -Me, -halo, —OH, —$NR_{17}R_{18}$. wherein each of said —$C_{3-4}$cycloalkyl is optionally and independently substituted with from 1 to 3 —H, -Me, -halo, —OH, —$NR_{17}R_{18}$;

More preferably, $R_8$ is selected from —$C_{1-3}$alkyl, —O—$C_{1-3}$alkyl, —$NR_{17}R_{18}$, —$C_{3-4}$cycloalkyl, —O—$C_{3-4}$cycloalkyl; wherein each of said —$C_{1-3}$alkyl is optionally and independently substituted with from 1 to 3 —H, -Me, -halo, —OH, —$NR_{17}R_{18}$. wherein each of said —$C_{3-4}$cycloalkyl is optionally and independently substituted with from 1 to 3 —H, -Me, -halo, —OH, —$NR_{17}R_{18}$.

Preferably, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$, and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$.

Preferably, $R_{27}$ and $R_{28}$, are each independently selected from —H, —$C_{1-6}$alkyl, —$C_{3-6}$cycloalkyl and -$Het_2$.

More preferably, $R_{27}$ and $R_{28}$, are each independently selected from —H, —$C_{1-3}$alkyl, or —$C_{3-4}$cycloalkyl; wherein each of said —$C_{1-3}$alkyl is optionally and independently substituted with from 1 to 3 —H, -Me, -halo; and wherein each of said —$C_{3-4}$cycloalkyl is optionally and independently substituted with from 1 to 3 —H, -Me, -halo.

Preferably, $R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$.

More preferably, $R_{37}$ and $R_{38}$, are each independently selected from —H, —$C_{1-3}$alkyl, or —$C_{3-4}$cycloalkyl; wherein each of said —$C_{1-3}$alkyl is optionally and independently substituted with from 1 to 3 —H, -Me, -halo; and wherein each of said —$C_{3-4}$cycloalkyl is optionally and independently substituted with from 1 to 3 —H, -Me, -halo, —OH.

Preferably, $X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$.

More preferably, $X_1$ is selected from —O—$C_{1-3}$alkyl, —$NR_3$—$C_{1-3}$alkyl-; wherein each of said —$C_{1-3}$alkyl is optionally and independently substituted with from 1 to 3 —H, -halo, —$CF_3$, $CHF_2$, —$C_{1-3}$alkyl, —C or substituted to form a cyclopropyl, cyclobutyl or oxetane; wherein each of said cyclopropyl, cyclobutyl or oxetane is optionally and independently substituted with from 1 to 3 —H, -Me, -halo, —OH Preferably, $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$.

More preferably, $X_2$ is selected from —O—$C_1$alkyl-, —$NR_2$—$C_1$alkyl; wherein each of said —$C_1$alkyl is optionally and independently substituted with from 1 to 2 —H, -halo, -Me or bi-substituted to form a cyclopropyl, cyclobutyl, oxetane; wherein each of said cyclopropyl, cyclobutyl or oxetane is optionally and independently substituted with from 1 to 3 —H, -Me, -halo, —OH Preferably, $Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, —$NR_{13}R_{20}$; wherein each of said —$C_{1-6}$alkyl is optionally and independently substituted with from 1 to 3 -halo.

More preferably, $Ar_1$, $Ar_4$, $Ar_5$, $Ar_6$, and $Ar_7$ are each independently selected from any 5 or 6 membered aromatic ring.

Preferably, $Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo.

More preferably, $Het_1$, $Het_2$, $Het_4$, $Het_5$, $Het_6$, and $Het_7$ are each independently selected from any 5 or 6 membered saturated or unsaturated heterocycle.

Preferably, $Het_8$ is a 3- to 10-membered heterocycle having from 1 to 3 heteroatoms selected from O, N and S;
  wherein said $Het_8$ is optionally and independently substituted with from 1 to 6 substituents selected from -halo, —OH, —$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;
  wherein when $R_1$ is —H, then at least one heteroatom of $Het_8$ is attached to $X_1$ More preferably, $Het_8$ is selected from piperidine or pyrrolidine, and optionally and independently substituted with from 1 to 6 substituents selected from —H, -halo, —OH, —$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo.

Preferably, $Z_1$, $Z_2$, $Z_3$, $Z_4$ and $Z_5$ are each independently selected from C and N.

More preferably, $Z_1$, $Z_2$, $Z_3$, $Z_4$ and $Z_5$ are each C.

In a further particular embodiment, the present invention provides a compound of Formula Ia or a stereoisomer, tautomer, racemic, metabolite, pro- or pre-drug, salt, hydrate, N-oxide form, or solvate thereof; wherein one or more of the following applies:

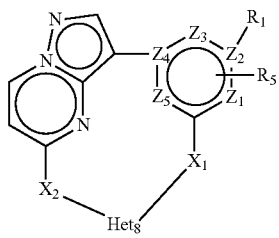

Ia $R_1$ is selected from —H, -halo, —OH, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{29}$, $R_{30}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_1$ $Z_1$, $Z_2$, $Z_3$, $Z_4$ and $Z_5$ are each independently selected from C and N.

In particular, $X_1$, and $X_2$ as used herein, represent biradicals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Referring to formula Ia:

$X_1$ is selected from the list comprising *—$C_{1-6}$alkyl-, *—O—$C_{1-6}$alkyl-, *—S—$C_{1-6}$alkyl-, *—$C_{1-6}$alkyl-$NR_3$—$C_{1-6}$alkyl-, *—$NR_3$—$C_{1-6}$alkyl-, *—$NR_3$—, *—O—; * wherein said biradical is preferably attached to the aryl or heteroaryl moiety via *;

$X_2$ is selected from the list comprising *—$C_{1-6}$alkyl-, *—O—$C_{1-6}$alkyl-, *—S—$C_{1-6}$alkyl-, *—$C_{1-6}$alkyl-$NR_2$—$C_{1-6}$alkyl-, *—$NR_2$—$C_{1-6}$alkyl-, *—$NR_2$—, *—O—; * wherein said biradical is preferably attached to the pyrazolopyrimidine moiety via *;

In still another embodiment, the present invention provides a compound of Formula Ia or a stereoisomer, tautomer, racemic, metabolite, pro- or pre-drug, salt, hydrate, N-oxide form, or solvate thereof; wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$ alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —C$_{1-6}$alkyl-NR$_3$—C$_{1-6}$alkyl-, —NR$_3$—C$_{1-6}$alkyl-, and —NR$_3$—;

X$_2$ is selected from —O—CH$_2$—, —S—CH$_2$—, and —NR$_2$—CH$_2$—;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

wherein when R$_1$ is —H, then at least one heteroatom of Het$_8$ is attached to X$_1$ Z$_1$, Z$_2$, Z$_3$, Z$_4$ and Z$_5$ are each independently selected from C and N.

In yet a further embodiment, the present invention provides a compound of Formula Ia or a stereoisomer, tautomer, racemic, metabolite, pro- or pre-drug, salt, hydrate, N-oxide form, or solvate thereof; wherein R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{36}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{29}$, R$_{30}$, R$_{31}$, R$_{32}$, R$_{33}$, R$_{34}$, R$_{37}$ and R$_{38}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{35}$R$_{36}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a bivalent 3- to 10-membered heterocycle having from 1 to 3 heteroatoms selected from O, N and S; wherein at least one of said heteroatoms is attached to X$_1$; and wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

In yet a further embodiment, the present invention provides a compound of Formula Ia or a stereoisomer, tautomer, racemic, metabolite, pro- or pre-drug, salt, hydrate, N-oxide form, or solvate thereof; wherein R$_1$ is selected from -halo, —C$_{1-6}$alkyl and —CN;
R$_5$ is attached to Z$_1$ and is selected from —H, -halo, —C$_{1-6}$alkyl, and —C$_{3-6}$cycloalkyl;
R$_2$ is selected from —H, —C$_{1-6}$alkyl and —C$_{3-6}$cycloalkyl;
X$_1$ is selected from —O—C$_{1-6}$alkyl, and —NR$_3$—C$_{1-6}$alkyl-;
X$_2$ is —NR$_2$—C$_{1-6}$alkyl;
Het$_8$ is a 3- to 10-membered N-containing heterocycle; and
Z$_1$, Z$_2$, Z$_3$, Z$_4$ and Z$_5$ are each C.

In yet a further embodiment, the present invention provides a compound of Formula Ia or a stereoisomer, tautomer, racemic, metabolite, pro- or pre-drug, salt, hydrate, N-oxide form, or solvate thereof; wherein R$_1$ and R$_5$ are both —H;
R$_2$ is selected from —H, —C$_{1-6}$alkyl and —C$_{3-6}$cycloalkyl;
X$_1$ is selected from —O—C$_{1-6}$alkyl, and —NR$_3$—C$_{1-6}$alkyl-;
X$_2$ is —NR$_2$—C$_{1-6}$alkyl;
Het$_8$ is a 3- to 10-membered N-containing heterocycle; wherein at least one of said heteroatoms is attached to X$_1$; and
Z$_1$, Z$_2$, Z$_3$, Z$_4$ and Z$_5$ are each C.

In yet a further embodiment, the present invention provides a compound of Formula Ia or a stereoisomer, tautomer, racemic, metabolite, pro- or pre-drug, salt, hydrate, N-oxide form, or solvate thereof; wherein R$_1$ is selected from —H and -halo;
R$_5$ is attached to Z$_1$ and is selected from —H, and -halo;
R$_2$ is selected from —H, and —C$_{1-6}$alkyl;
X$_1$ is —O—C$_{1-6}$alkyl;
X$_2$ is —NR$_2$—C$_{1-6}$alkyl;

Het$_8$ is a 5- to 6-membered N-containing heterocycle; wherein when R$_1$ is —H, then at least one of said heteroatoms is attached to X$_1$; and Z$_1$, Z$_2$, Z$_3$, Z$_4$ and Z$_5$ are each C.

In a particular embodiment, the present invention provides a compound selected from the list comprising:

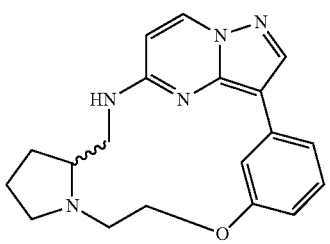

Compound O1, Example O1

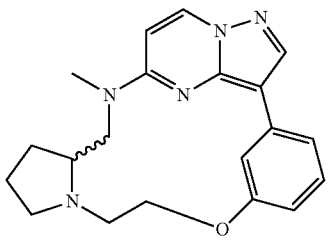

Compound O2, Example O2

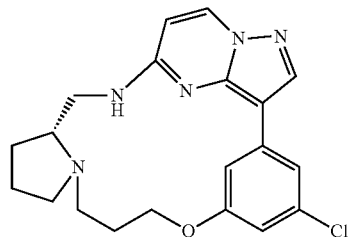

Compound O3, Example O3

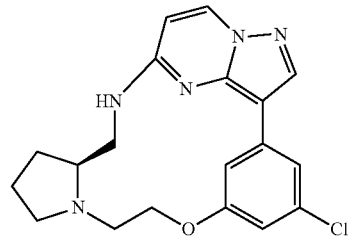

Compound O4, Example O4

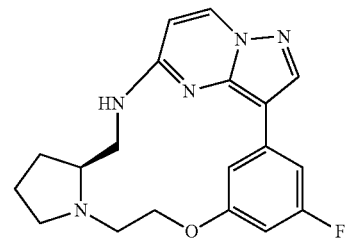

Compound O5, Example O5

Compound O6, Example O6

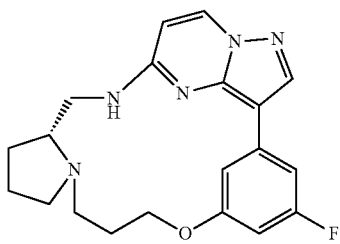

Compound O7, Example O7

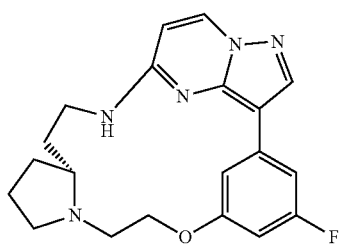

Compound O8, Example O8

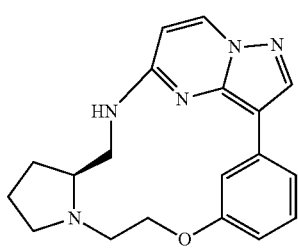

Compound O9, Example O9

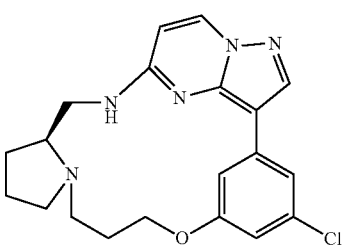

Compound O10, Example O10

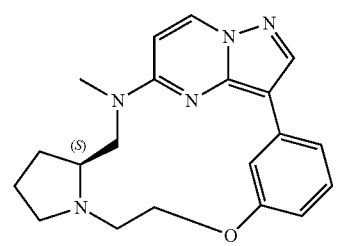

Compound O11, Example O11

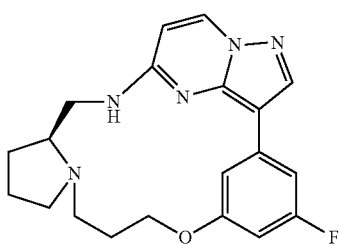

Compound O12, Example O12

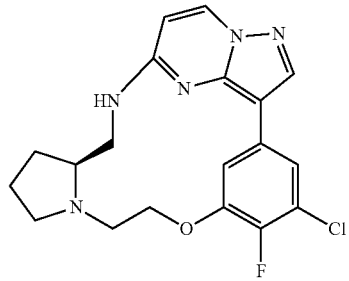

Compound O13, Example O13

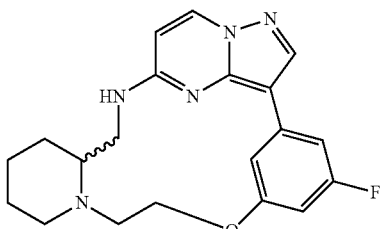

Compound O14, Example O14

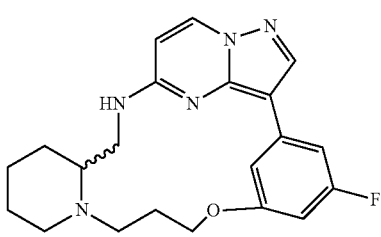

In particular in the compounds according to this invention, the $R_5$ is linked to the aryl or heteroaryl moiety at position $Z_1$ in accordance with the numbering as provided in Formula I or Ia.

Furthermore, the present invention provides a compound according to this invention, wherein said compound is the S-enantiomer.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

The present invention further provides a pharmaceutical composition comprising a compound according to this invention.

In a further aspect, the present invention provides a compound or a composition according to this invention, for use as a medicine.

In a particular embodiment, the present invention provides a compound or composition according to this invention for use in the diagnosis, prevention and/or treatment of a RIP2-kinase associated disease. Said RIP2-kinase associated disease may in particular be an inflammatory disorders, more in particular selected from the list comprising: Crohn's disease, bowel disease, Sarcoidosis, psoriasis, rheumatoid arthritis, asthma, ulcerative colitis, lupus, uveitis, blau syndrome, granulomatous inflammation, in particular behget's disease, multiple sclerosis and insulin-resistant type 2 diabetes.

Furthermore, the present invention provides the use of a compound or composition according to this invention, suitable for inhibiting the activity of a kinase; in particular a RIP2 kinase; or for the diagnosis, prevention and/or treatment of a RIP2-kinase associated disease.

Finally, the present invention provides a method for prevention and/or treatment of a RIP2-kinase associated disease; said method comprising administering to a subject in need thereof a compound or a composition according to the present invention.

Method of Treatment

Compounds of formula (I) or (Ia) a stereoisomer, tautomer, racemic, metabolite, pro- or pre-drug, salt, hydrate, N-oxide form, or solvate thereof, are inhibitors of RIP2 kinase activity and are thus believed to be of potential use in the diagnosis, prevention and/or treatment of inflammatory disorders, in particular Crohn's disease, bowel disease, Sarcoidosis, psoriasis, rheumatoid arthritis, asthma, ulcerative colitis, lupus, uveitis, blau syndrome, granulomatous inflammation, in particular behget's disease, multiple sclerosis and insulin-resistant type 2 diabetes.

As used herein, the terms "inflammatory disorder" or "inflammatory disease" can refer to a disorder or disease characterized by aberrant activation of the immune system that leads to or causes pathogenesis of several acute and chronic conditions including, for example, sarcoidosis, rheumatoid arthritis, inflammatory bowel disease, transplant rejection, colitis, gastritis and ileitis. An inflammatory disease can include a state in which there is a response to tissue damage, cell injury, an antigen, an infectious disease, and/or some unknown cause. Symptoms of inflammation may include, but are not limited to, cell infiltration and tissue swelling.

In the invention, particular preference is given to compounds of Formula I or any subgroup thereof that in the inhibition assay for RIP2 described below inhibit kinase activity with an $IC_{50}$ value of less than 10 µM, preferably less than 1 µM, most preferably less than 100 nM.

Said inhibition may be effected in vitro and/or in vivo, and when effected in vivo, is preferably effected in a selective manner, as defined above.

The term "RIP2 kinase-mediated condition" or "disease", as used herein, means any disease or other deleterious condition in which the RIP2 kinase and/or mutants thereof is/are known to play a role. The term "RIP2 kinase-mediated condition" or "disease" also means those diseases or conditions that are alleviated by treatment with a RIP2 kinase inhibitor. Accordingly, another embodiment of the present invention relates to treating or lessening the severity of one or more diseases in which the RIP2 kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethylbromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For local administration, the compounds may advantageously be used in the form of a spray, ointment or transdermal patch or another suitable form for topical, transdermal and/or intradermal administration.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringers solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used orally or parenterally.

The invention will now be illustrated by means of the following synthetic and biological examples, which do not limit the scope of the invention in any way.

EXAMPLES

A. Compound Synthesis and Physicochemical Properties

The compounds of this invention can be prepared by any of several standard synthetic processes commonly used by those skilled in the art of organic chemistry. The compounds are generally prepared from starting materials which are either commercially available or prepared by standard means obvious to those skilled in the art.

General Schemes:

As indicated herein before, the present invention in general provides compounds according to formula I, for use in the diagnosis, prevention and/or treatment of RIP2-kinase associated diseases:

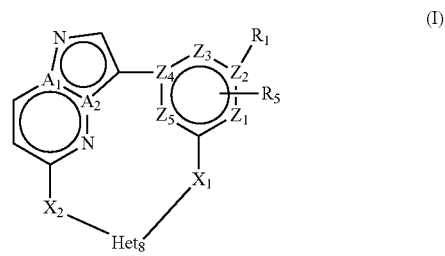

(I)

With reference to the general reaction schemes suitable for preparing said compounds, these compounds can be represented by formulas Ia or Ib respectively, for which the general reaction schemes can be found herein below.

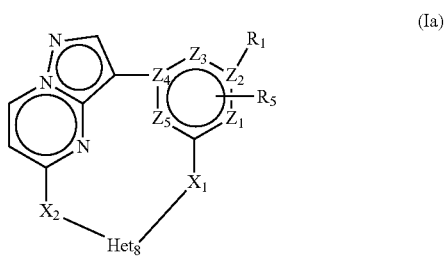

(Ia)

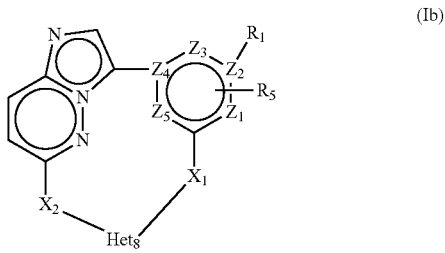

(Ib)

In general the compounds of formula (I) can be prepared as shown in scheme 1 below wherein a pyrazolo[1,5-a]pyrimidine or a imidazo[2,1-f]pyridazine of formula (II) is converted by reaction with a compound of formula (VII) into a compound of formula (VIII). The compound of formula (VIII) can be optionally be converted into a compound of formula (IV) which is then reacted with a (hetero-)aryl of formula (V) to form a compound of formula (VI). The compound of formula (VI) can be optionally converted into a compound of general formula (I).

Scheme 1

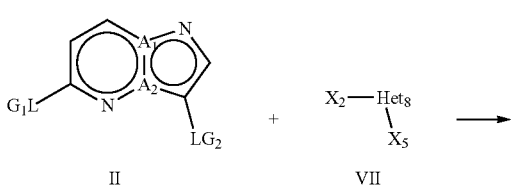

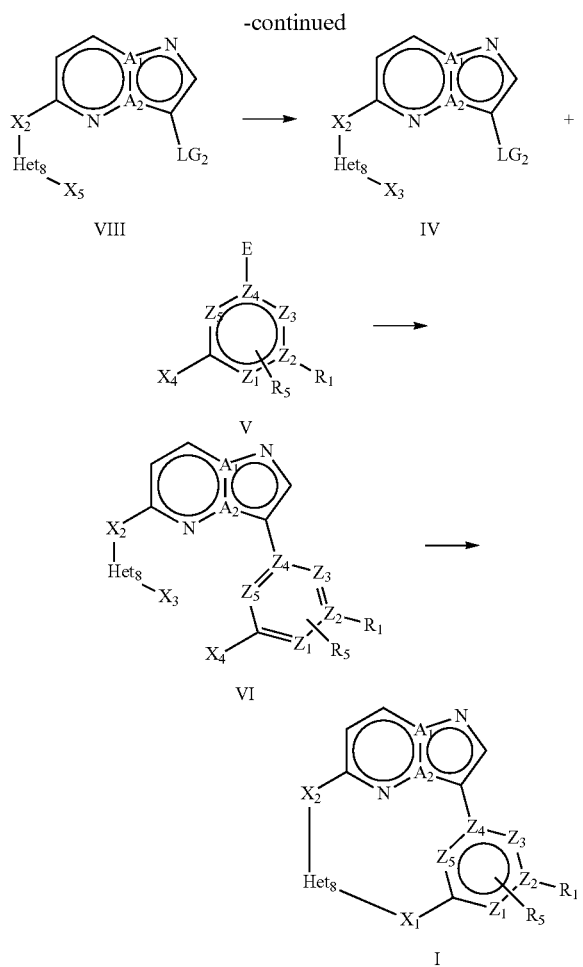

derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example under reflux.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C.

The free hydroxyl group could also be converted into a leaving group such as a chloride by reacting the hydroxyl group for example with thionyl chloride in the presence of a base such as pyridine in a solvent such as dichloromethane at an elevated temperature for example under reflux.

The cyclisation of the compound of formula (VI) can be advantageously effected under Williamson conditions for example using a base such as cesium carbonate in a solvent such as N,N-dimethylformamide at an elevated temperature such as 90° C. resulting in the formation of compound of formula (I).

The resulting compound of formula (I) can optionally be treated to introduce a substituents such as an alkyl group.

Compounds O1, O2, O3, O4, O5, O6, O7, O8, O9, O10, O11, O12, O13 and O14 may be prepared according to the synthesis described in Scheme 1.

Experimental Part

In obtaining the compounds described in the examples, the following experimental protocols were followed unless otherwise indicated.

In the above scheme:

$LG_1$ and $LG_2$ each independently represent suitable leaving or functional groups;

$X_5$ is converted into a functional group $X_3$;

$X_3$ and $X_4$ together with the functional moiety to which they are attached represent an unprotected or a protected functional group which upon reaction (after deprotection) produce together $X_1$ as defined in formula I;

E represents a suitable functional group that can be used to form a direct bond between the (hetero-)aryl group and the scaffold.

In the above reaction of the compound of formula (II) with the compound of formula (VII) the leaving groups $LG_1$ and $LG_2$ are advantageously a halo group such as a chlorine or a bromine group. The reaction can be affected by a substitution for example by treating the compound of formula (II) with the compound of formula (VII) in an organic solvent such as acetonitrile with an appropriate base such as for example triethylamine at an elevated temperature for example under reflux.

Compounds of formula (VII) can be obtained through various selective reaction steps by standard means obvious to those skilled in the art.

Compounds of formula (VIII) can be converted to compounds of formula (IV) by reaction with a suitable protected or unprotected linker group.

The reaction of the compound (IV) with a (hetero-)aryl compound of formula (V) is advantageously effected through the coupling of a boronic acid E or boronic ester E Unless otherwise stated, reaction mixtures were magnetically stirred at room temperature. Where solutions were "dried", they were generally dried over a drying agent such as sodium sulfate or magnesium sulfate. Where mixtures, solutions and extracts were "concentrated", they were typically concentrated on a rotary evaporator under reduced pressure.

For some compounds that were purified by reversed phase high-performance liquid chromatography (HPLC) the used method is described below (indicated in the compound procedure with HPLC method A). When necessary, these methods can be slightly adjusted by a person skilled in the art to obtain a more optimal result for the separation.

HPLC Method A

The crude product was purified by reverse phase HPLC, using a Gilson semi-preparative HPLC system operated by Gilson UNIPOINT software.

The purification was carried out on a Phenomenex Luna column (100 mm long×21.2 mm i.d.; 5 μm particles) at room temperature, with a constant flow rate of 20.0 mL/min. A gradient elution was performed from 32% (25 mM NH4HCO3 aqueous solution)/68% (Acetonitrile-Methanol 1:1) to 4% (25 mM NH4HCO3 aqueous solution)/96% (Acetonitrile-Methanol 1:1) in 20 minutes. The UV detector was set to 226 nm, which corresponds to the wavelenght of maximum absorbance observed for the compound.

Example O1

Example O1 was prepared following general scheme 1

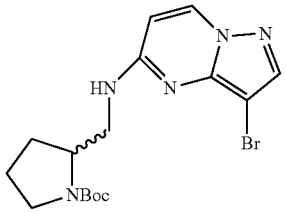 [SMILES: CC(C)(C)OC(=O)N1CCCC1CNc1ccn2ncc(Br)c2n1]

Step A 3-bromo-5-chloropyrazolo[1,5-a]pyrimidine (2.32 g, 9.998 mmol, 1.0 eq), tert-butyl 2-(aminomethyl)pyrrolidine-1-carboxylate (2.0 g, 9.98 mmol, 1.0 eq) and triethylamine (2.26 ml, 12.97 mmol, 1.3 eq) were suspended in MeCN (30 ml). The reaction mixture was heated at 80° C. for 5 h. Upon completion, monitored by TLC plate, solvent was evaporated. The residue was dissolved in EtOAc and washed with aqueous 1 N HCl, aqueous 1N NaHCO3. The organic layer was dried (MgSO4), filtered and concentrated to dryness. The crude was purified by flash chromatography using the following eluent: Heptane:EtOAc 100:0 to 75:25 fast tot 50:50 slow. The title compound was obtained as a solid in 3.32 g (84% yield).

MH+: 396.1/398.1

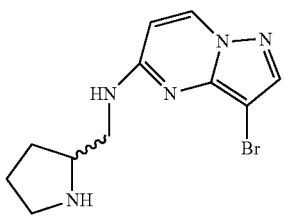 [SMILES: Brc1cnn2ccc(NCC3CCCN3)nc12]

Step B

The title compound from step A was stirred in 25 ml of HCl 4M in MeOH for 18 h at RT. Upon completion, monitored by LCMS, solids were filtered off and washed with a small amount of MeOH yielding a first fraction of yellowish solid (1.6 g). The mother liquor was concentrated yielding a second fraction of a brownish solid (1.5 g). The title compound was obtained in 3.1 g (110%).

MH+: 296.1/298.1

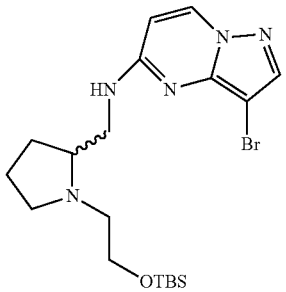 [SMILES: CC(C)(C)[Si](C)(C)OCCN1CCCC1CNc1ccn2ncc(Br)c2n1]

Step C

The title compound from step B (2.6 g, 7.82 mmol, 1.0 eq), (2-bromoethoxy)(tert-butyl)dimethylsilane (2.02 ml, 9.38 mmol, 1.2 eq) and Potassium carbonate (3.24 g, 23.46 mmol, 3.0 eq) were suspended in CH3CN and heated at 90° C. for 1 h. Then an additional 1.2 eq of (2-bromoethoxy)(tert-butyl)dimethylsilane was added and the reaction mixture was stirred for 1 h at 90° C. Upon completion, monitored by TLC plate, the reaction mixture was concentrated. The residue was dissolved in EtOAc and washed with water 2× and Brine. The organic layer was dried (MgSO4), filtered, concentrated. The crude was purified by flash chromatography using the following eluent: DCM:MeOH 99:1 to 90:1. The product fractions were collected and concentrated to lead 2.2 g of a solid (62%).

MH+: 454.3/456.3

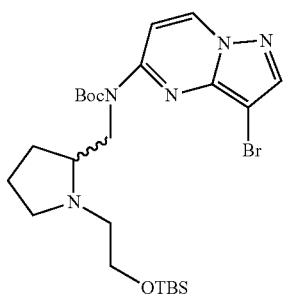 [SMILES: CC(C)(C)OC(=O)N(CC1CCCN1CCO[Si](C)(C)C(C)(C)C)c1ccn2ncc(Br)c2n1]

Step D

The title compound from step C (2.2 g, 4.84 mmol, 1.0 eq), Boc anhydride (1.16 g, 5.32 mmol, 1.1 eq) and DMAP (0.029 g, 0.24 mmol, 0.05 eq) were dissolved in THF (14 ml) and stirred for 1 h at rt then at 65° C. for 1 h. Additional Boc anhydride was added and the reaction was stirred for an additional 1 h at 65° C. Upon completion, monitored by TLC plate, the reaction mixture was concentrated.

The crude was purified by flash chromatography using the following eluent: Heptane:EtOAC 100:0 to 50:50 fast to lead the title compound in 2.1 g (78% yield).

MH+: 606.2/608.3

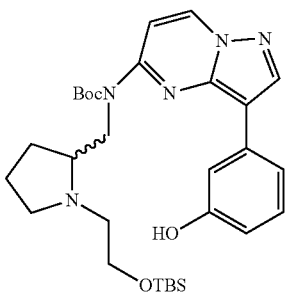 [SMILES: CC(C)(C)OC(=O)N(CC1CCCN1CCO[Si](C)(C)C(C)(C)C)c1ccn2ncc(-c3cccc(O)c3)c2n1]

Step E

A mixture of the title compound from step D (2.1 g, 3.79 mmol, 1.0 eq), (3-hydroxyphenyl)boronic acid (0.68 g, 4.93 mmol, 1.3 eq), XPhos (0.072 g, 0.15 mmol, 0.04 eq) and Potassium phosphate (2.41 g, 11.35 mmol, 3.0 eq) were dissolved in Dioxane/water 3:1 (12 ml) and degassed with N2. Palladium tetrakis (0.093 g, 0.08 mmol, 0.02 eq) was added to the stirring mixture, which was warmed to 85° C. for 3 h under N2 atmosphere. Upon completion, monitored by TLC plate, the reaction mixture was diluted with EtOAc. Layers separated, organic layer was washed with water and Brine, dried (MgSO4), concentrated to dryness. The crude was purified by flash chromatography using the following eluent: DCM:MeOH 100:0 to 97.5:2.5. Product fractions collected and concentrated to dryness to lead the title compound in 1.98 g (92% yield).

MH+: 568.4

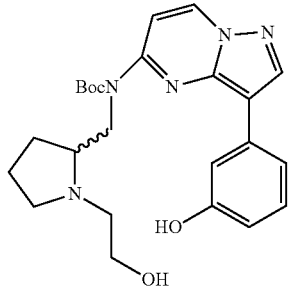 [SMILES: CC(C)(C)OC(=O)N(CC1CCCN1CCO)c1ccn2ncc(-c3cccc(O)c3)c2n1]

Step F

The title compound from step E (1.98 g, 3.49 mmol, 1.0 eq) was dissolved in THF (10 ml), then TBAF 1M in THF (3.84 ml, 1.1 eq) was added. The reaction mixture was stirred for 2 h at RT.

TLC: SM A present. Stirred additional 1 h at rt. Upon completion, monitored by LCMS, solvent was evaporated and the residue was dissolved in EtOAc and washed with aq. sat. NaHCO3 3×. The organic layer was dried (MgSO4), filtered, concentrated to dryness.

The crude was purified by flash chromatography using the following eluent: DCM:MeOH 100:0 to 97:3 to 93:7 to obtain the title compound in 1.1 g (69% yield).

MH+: 454.3

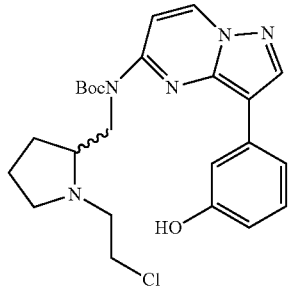 [SMILES: CC(C)(C)OC(=O)N(CC1CCCN1CCCl)c1ccn2ncc(-c3cccc(O)c3)c2n1]

Step G

In a pre-dried flask, to a stirred solution of the title compound from step F (0.62 g, 1.37 mmol, 1.0 eq) and Pyridine (0.335 ml, 4.11 mmol, 3.0 eq) in anhydrous DCM (6 ml) at 0° C. under N2 atmosphere was added Thionyl chloride (0.3 ml, 4.11 mmol, 3.0 eq). After addition the reaction was stirred for 30 min at 0° C. and then for 2 hours at RT under N2 atmosphere. The reaction mixture was concentrated and co-evaporated with toluene/DCM mixture 2× and once with toluene yielding orange/brown solids. The crude was used as such in the next step.

MH+: 436.2

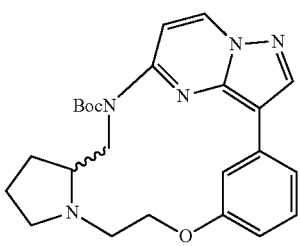 [SMILES: CC(C)(C)OC(=O)N1CC2CCCN2CCOc2cccc(c2)-c2cnn3ccc1nc23]

Step H

To a stirred suspension of Cesium carbonate (2.23 g, 6.85 mmol, 5.0 eq) in DMF (103 ml; 75 ml/mmol, calculated from the title compound of step G) at 90° C. was added a solution of the title compound from step G (1.37 mmol) in 34 ml DMF (25 ml/mmol) dropwise over 2 h. Then the reaction was stirred at 90° C. for 1 hour. Upon completion, monitored by LCMS, DMF was reduced under vacuum. The residue was diluted with DCM (emulsion) and washed with water once. The organic layer was concentrated to dryness. The crude was purified by flash chromatography using the following eluent: Heptane:EtOAc 100:0 to 60:40 to lead the title compound in 350 mg (58% yield over 2 steps).

MH+: 436.2

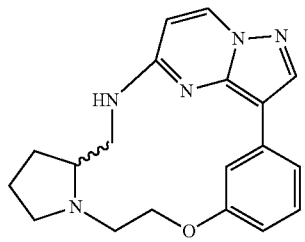 [SMILES: c1cc2cc(c1)-c1cnn3ccc(nc13)NCC1CCCN1CCO2]

Step I

The title compound from step H (350 mg, 0.8 mmol, 1.0 eq) was stirred in HCl 4M in MeOH (5 ml) for 77 h at RT. Upon completion, monitored by LCMS, the white solids were filtered off and washed with MeOH and dried at 45° C. under vacuum to lead the first fraction. The mother liquor was concentrated and co-evaporated with EtOH. During the co-evaporation and white solid crushed out which was collected and washed with MeOH and Ether, dried at 45° C. under vacuum to lead a second fraction. The fractions were combined to lead a white solid in 246 mg (91% yield)

MH+: 366.1

Melting point>300° C.

HPLC retention time: 0.443 min

Examples O3 to O9 and O11 to O14 were prepared following general scheme 1 and according to the procedures described in the Example O1.

Example O2

Example O2 was prepared following the general scheme 1

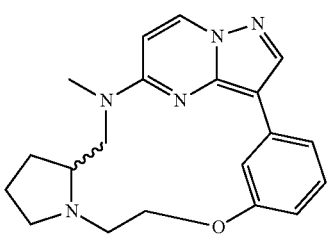 [SMILES: CN1CC2CCCN2CCOc2cccc(c2)-c2cnn3ccc1nc23]

Step A

In a pre-dried flask, the title compound from Example O1 (82 mg, 0.22 mmol, 1.0 eq) was dissolved in 1 ml anhydrous DMF. Sodium hydride 60% (50 mg, 2.2 mmol, 10.0 eq) was added. The reaction mixture was stirred for 30 min at rt (solution), then Methyl iodide (16 ul, 0.25 mmol, 1.15 eq)

was added. The reaction mixture was stirred for 1 h at rt. LCMS monitoring showed a mixture of the expected product and dimethylated product. The reaction mixture was quenched with water. The product was extracted with DCM:MeOH 9:1 twice. The organic layer was dried (MgSO4), filtered, concentrated. The crude was purified by flash chromatography in DCM:MeOH 100:0 to 96:4. The resulting oil was triturated with DIPE and DCM and concentrated twice to lead the title compound in 25 mg (32% yield).

MH+: 350.2

Retention time: 2.154 min

Melting point: 91.2° C.

Example O10

Example O10 was prepared following the general scheme 1, more precisely following a similar procedure than for the preparation of Example O2.

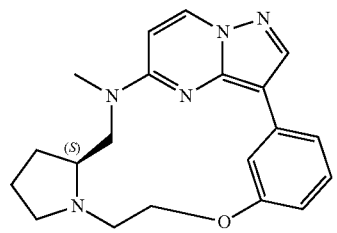

MH+: 350.2

Retention time: 1.912 min

Melting point: 198.5° C.

TABLE 1

| | |
|---|---|
| 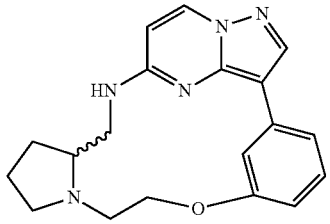 [SMILES: c1cc2cc(c1)-c1cnn3ccc(nc13)NCC1CCCN1CCO2] | Compound O1, Example O1 |
| 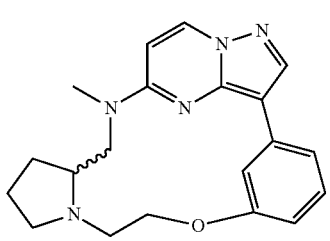 [SMILES: CN1CC2CCCN2CCOc2cccc(c2)-c2cnn3ccc1nc23] | Compound O2, Example O2 |
| 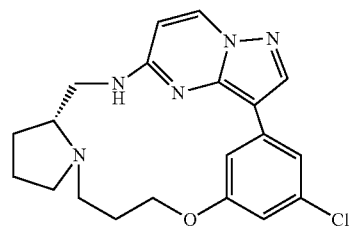 [SMILES: Clc1cc2cc(c1)-c1cnn3ccc(nc13)NC[C@H]1CCCN1CCCO2] | Compound O3, Example O3 |

TABLE 1-continued

| | |
|---|---|
| 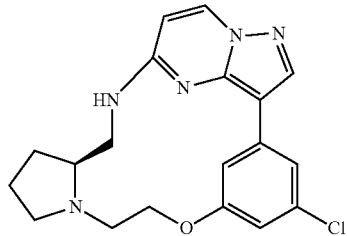 [SMILES: Clc1cc2cc(c1)-c1cnn3ccc(nc13)NC[C@@H]1CCCN1CCO2] | Compound O4, Example O4 |
| 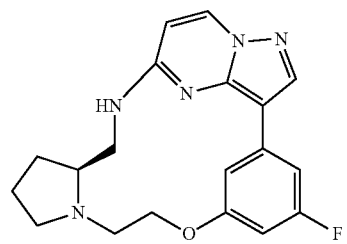 [SMILES: Fc1cc2cc(c1)-c1cnn3ccc(nc13)NC[C@@H]1CCCN1CCO2] | Compound O5, Example O5 |
| 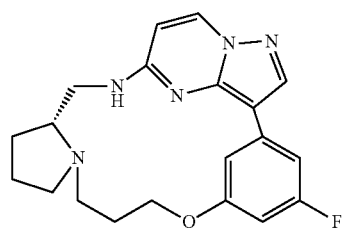 [SMILES: Fc1cc2cc(c1)-c1cnn3ccc(nc13)NC[C@H]1CCCN1CCCO2] | Compound O6, Example O6 |
| 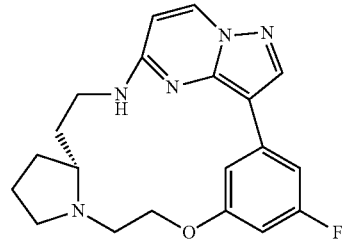 [SMILES: Fc1cc2cc(c1)-c1cnn3ccc(nc13)NCC[C@H]1CCCN1CCO2] | Compound O7, Example O7 |
| 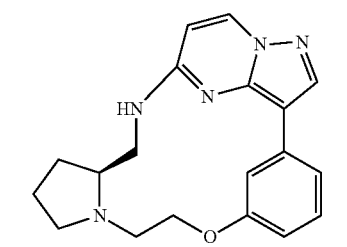 [SMILES: c1cc2cc(c1)-c1cnn3ccc(nc13)NC[C@@H]1CCCN1CCO2] | Compound O8, Example O8 |
| 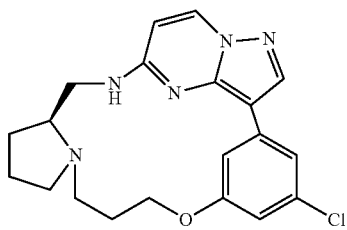 [SMILES: Clc1cc2cc(c1)-c1cnn3ccc(nc13)NC[C@@H]1CCCN1CCCO2] | Compound O9, Example O9 |

TABLE 1-continued

| | |
|---|---|
| 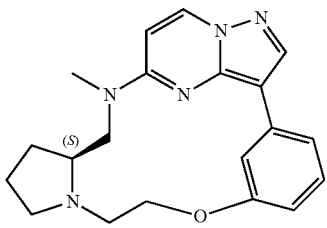 | Compound O10, Example O10 |
| 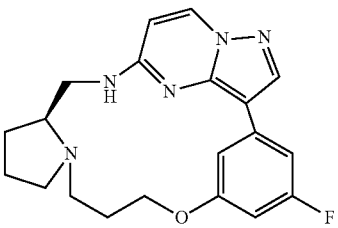 [SMILES: Fc1cc2cc(c1)-c1cnn3ccc(nc13)NC[C@@H]1CCCN1CCCO2] | Compound O11, Example O11 |
| 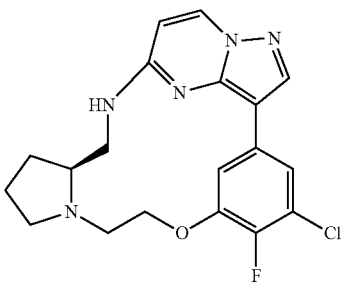 [SMILES: Fc1c(Cl)cc2cc1OCCN1CCC[C@H]1CNc1ccn3ncc-2c3n1] | Compound O12, Example O12 |
| 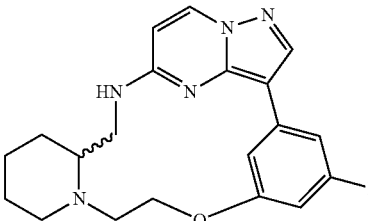 | Compound O13, Example O13 |
| 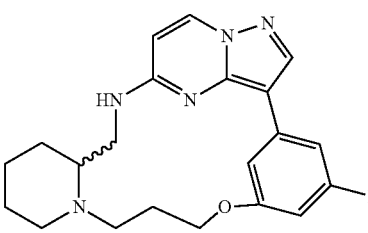 | Compound O14, Example O14 |

The compounds were identified according to the analytical methods and the analytical results described in WO02013/045653 A1 and WO2013/046029 A1.

TABLE 2

Melting points

| COMPOUND N° | MELTING POINT (° C.) |
|---|---|
| O1 | >300 |
| O2 | 91.2 |
| O3 | 186.4 |
| O4 | >300 |
| O5 | 241 |
| O6 | >300 |
| O7 | >300 |
| O8 | >300 |
| O9 | >300 |
| O10 | 198.5 |
| O11 | >300 |
| O12 | 273.8 |
| O13 | 298.4 |
| O14 | >300 |

TABLE 3

LCMS data

| COMPOUND NUMBER | MASS (MH)+ PEAK | RETENTION TIME (min) | LCMS METHOD |
|---|---|---|---|
| O1 | 336.2 | 2.044 | 2 |
| O2 | 350.2 | 2.154 | 2 |
| O3 | 384.0 | 2.232 | 2 |
| O4 | 369.9 | 2.188 | 2 |
| O5 | 354.1 | 1.966 | 2 |
| O6 | 368.0 | 2.041 | 2 |
| O7 | 368.0 | 1.998 | 2 |
| O8 | 336.1 | 1.841 | 2 |
| O9 | 384.1 | 2.22 | 2 |
| O10 | 350.2 | 1.912 | 2 |
| O11 | 368.1 | 2.052 | 2 |
| O12 | 388.0 | 2.212 | 2 |
| O13 | 368.0 | 2.055 | 2 |
| O14 | 382.2 | 2.247 | 2 |

The inhibition of RIP2 kinase was assessed using RIP2 recombinant protein in an in vitro peptide-based kinase assay.

B. Kinase Activity Assay

The inhibition of RIP2 kinase was assessed using RIP2 recombinant protein in an in vitro peptide-based kinase assay.

Protocol

A radiometric protein kinase assay ($^{33}$PanQinase® Activity Assay) is used for measuring the kinase activity. All assays are performed in 96-well FlashPlates™ from Perkin Elmer in a 50 μl reaction volume. The reaction cocktail is pipetted in 4 steps in the following order:

10 μl of non-radioactive ATP solution (in H2O)
25 μl of assay buffer/[γ-$^{33}$P]-ATP mixture
5 μl of test sample in 10% DMSO
10 μl of enzyme/substrate mixture The assay for RIP2 contains 70 mM HEPES-NaOH pH 7.5, 3 mM MgCl$_2$, 3 mM MnCl$_2$, 3 μM Na-orthovanadate, 1.2 mM DTT, 50 μg/ml PEG20000, ATP (3.0 μM), [γ-$^{33}$P]-ATP (approx. 5×10$^{05}$ cpm per well), protein kinase RIP2 (15.7 nM) and substrate (RBER-Chktide), 2.0 μg/50 μl).

The reaction cocktails were incubated at 30° C. for 60 minutes. The reaction was stopped with 50 μl of 2% (v/v) H$_3$PO$_4$, plates were aspirated and washed two times with 200 μl 0.9% (w/v) NaCl. Incorporation of $^{33}$Pi (counting of "cpm") was determined with a microplate scintillation counter.

Compounds

The compounds are dissolved to 10 mM in DMSO. Where needed, solutions are sonicated in a bath sonicator.

Table 4 provides the pIC$_{50}$ values and % Remaining activity values at two concentrations (1 μM and 0.1 μM) of the compounds according to the invention, obtained using the above mentioned kinase assay.

TABLE 4

| | RIP2 biochemical affinity | | |
|---|---|---|---|
| Compound N° | IC$_{50}$ for RIP2 | % Remaining RIP2 activity at 1 μM | % Remaining RIP2 activity at 0.1 μM |
| O1 | +++ | ** | ** |
| O2 | +++ | ND | ND |
| O3 | +++ | ** | ** |
| O4 | +++ | ** | ** |
| O5 | +++ | ** | ** |
| O6 | +++ | ** | ** |
| O7 | +++ | ** | ** |
| O8 | +++ | ** | ** |
| O9 | +++ | ** | ** |
| O10 | +++ | ** | ** |
| O11 | +++ | ** | ** |
| O12 | +++ | ** | ** |
| O13 | +++ | ** | ** |
| O14 | +++ | ND | ND |

+indicates an IC50 > 1 μM,
++indicates an IC50 of between 100 nM and 1 μM, and
+++indicates an IC50 < 100 nM
* indicates a % remaining kinase activity above 50%,
** indicates a % remaining kinase activity below 50%
ND = Not determined

The invention claimed is:
1. A compound of Formula Ia or a stereoisomer, tautomer, racemic, salt, or N-oxide form thereof,

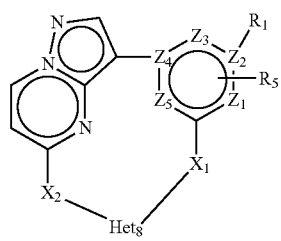

Wherein:
$R_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$, and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

$R_5$ is attached to $Z_1$ or $Z_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

$R_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

$R_3$ is selected from —H, -halo, —OH, —C$_{1-6}$alkyl, and —C$_{3-6}$cycloalkyl; wherein each of said-C$_{1-6}$alkyl is optionally and independently substituted with from 1 to 3 substituents selected from -halo, —OR$_{28}$, and —NR$_{15}$R$_{16}$;

$R_4$ and $R_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{29}$, $R_{30}$, $R_{31}$, $R_{32}$, $R_{33}$, $R_{34}$, $R_{37}$, and $R_{38}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$ alkyl, —C$_{3-6}$cycloalkyl, -Het$_6$, —Ar$_6$ and —NR$_{35}$R$_{36}$;

$R_{27}$ and $R_{28}$, are each independently selected from —H, —C$_{1-6}$alkyl, —C$_{3-6}$cycloalkyl and -Het$_2$;

$R_{37}$ and $R_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

$X_1$ is selected from —C$_{1-6}$alkyl-, —O—C$_{1-6}$alkyl, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ $X_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, —phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is pyrrolidine or piperidine; and
$Z_1$, $Z_2$, $Z_3$, $Z_4$ and $Z_5$ are each C.

2. A compound as defined in claim 1, wherein:
$R_1$ is selected from —H, -halo, —OH, —C$_{1-6}$ alkyl, —O—C$_{1-6}$ alkyl, —S—C$_{1-6}$ alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$ cycloalkyl, —O—C$_{3-6}$ cycloalkyl, —Ar$_1$, and -Het$_1$; wherein each of said —C$_{1-6}$ alkyl is optionally and independently substituted with from 1 to 3 substituents selected from -halo, —OR$_{35}$, —NR$_{11}$R$_{12}$, —O—C$_{1-6}$ alkyl, and —S—C$_{1-6}$ alkyl;

$R_5$ is attached to $Z_1$ or $Z_5$ and is selected from —H, -halo, —OH, —$C_{1-6}$ alkyl, —O—$C_{1-6}$ alkyl, —S—$C_{1-6}$ alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$ cycloalkyl, —$Ar_5$ and -$Het_5$; wherein each of said —$C_{1-6}$ alkyl is optionally and independently substituted with from 1 to 3 substituents selected from -halo, —$OR_{36}$, —$NR_{23}R_{24}$, —O—$C_{1-6}$ alkyl, and —S—$C_{1-6}$ alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$ alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$ cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$ alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, and —$NR_3$—;

$X_2$ is selected from —O—$CH_2$—, —S—$CH_2$—, and —$NR_2$—$CH_2$—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$ alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$ alkyl is optionally and independently substituted with from 1 to 3 -halo;

$Het_8$ is pyrrolidine or piperidine; and $Z_1$, $Z_2$, $Z_3$, $Z_4$ and $Z_5$ are each C.

3. A compound as defined in claim 1, wherein:

$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$, and -$Het_1$; wherein each of said —$C_{1-6}$ alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{29}$, $R_{30}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$ alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$ alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, $NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$ alkyl-, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$ alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is pyrrolidine or piperidine; and $Z_1$, $Z_2$, $Z_3$, $Z_4$ and $Z_5$ are each C.

4. A compound as defined in claim 1,

Wherein:

$R_1$ is selected from -halo, —$C_{1-6}$alkyl, and —CN;

$R_5$ is attached to $Z_1$ and is selected from —H, -halo, —$C_{1-6}$alkyl, and —$C_{3-6}$cycloalkyl;

$R_2$ is selected from —H, —$C_{1-6}$alkyl and —$C_{3-6}$cycloalkyl;

$X_1$ is selected from —O—$C_{1-6}$alkyl, and —$NR_3$—$C_{1-6}$alkyl-;

$X_2$ is $NR_2$—$C_{1-6}$alkyl;

$Het_8$ is pyrrolidine or piperidine; and $Z_1$, $Z_2$, $Z_3$, $Z_4$ and $Z_5$ are each C.

5. A compound as defined in claim 1, said compound being selected from:

Compound O1

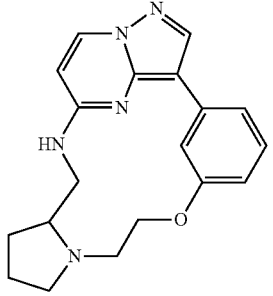

Compound O2

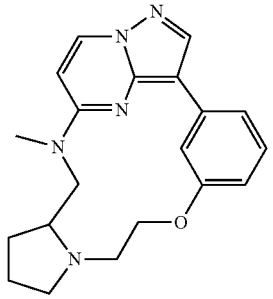

Compound O3

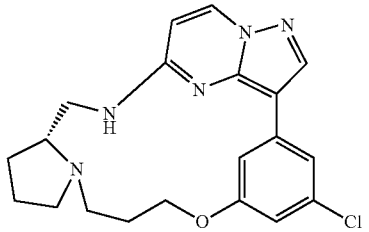

Compound O4

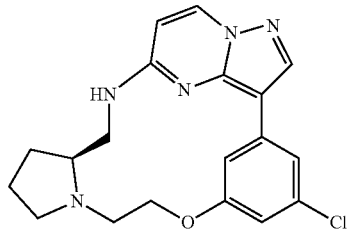

Compound O5

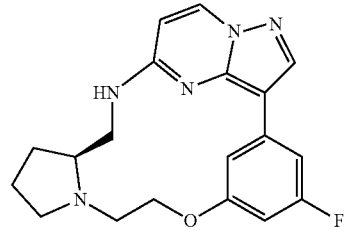

Compound O6

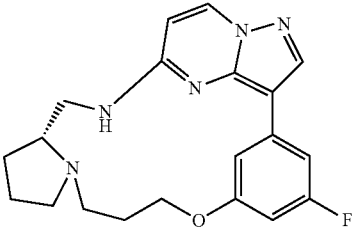

Compound O7

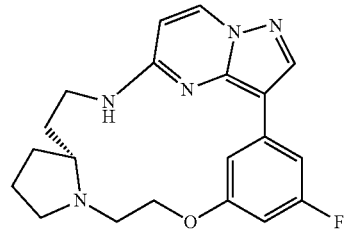

Compound O8

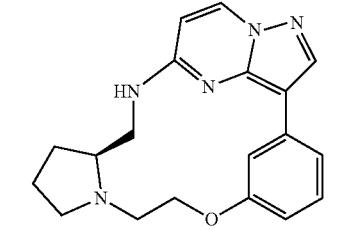

Compound O9

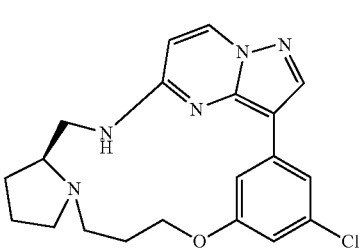

-continued

Compound O10
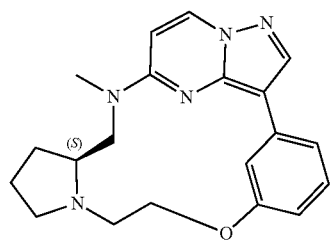

Compound O11
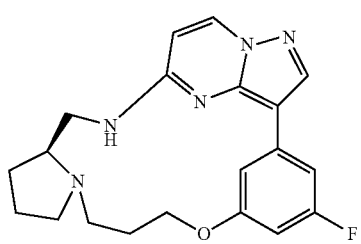

Compound O12
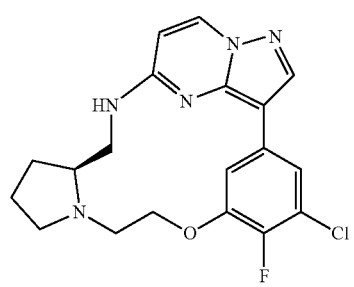

Compound O13
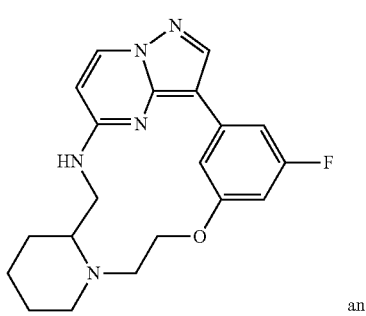

and

Compound O14
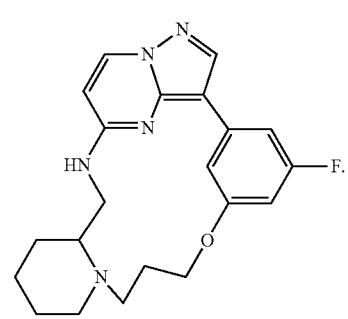

6. A compound according to 1; wherein $R_5$ is linked to the aryl moiety at position $Z_1$ in accordance with the numbering as provided in Formula Ia.

7. A compound according claim 1; wherein said compound is the S-enantiomer.

8. A pharmaceutical composition comprising a compound according to claim 1 at least one pharmaceutically acceptable carrier, diluent, or excipient.

9. A compound as defined in claim 1, wherein:

$R_1$ is selected from —F, —Cl, —CN, —O—$C_{1-6}$alkyl, and —O—$C_{1-6}$cycloalkyl; wherein each of said —$C_{1-6}$ alkyl is optionally and independently substituted with from 1 to 3 -Me, -halo, —OH, —H, -cyclopropyl, or -cyclobutyl; -cycloalkyls are optionally independently substituted by -Me, -halo, —OH, or —H;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{29}$, $R_{30}$, $R_{31}$, $R_{32}$, $R_{33}$, $R_{34}$, $R_{37}$ and $R_{38}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$ alkyl, —$C_{3-6}$cycloalkyl, -$Het_6$, —$Ar_6$ and —$NR_{35}R_{36}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$ alkyl, —$C_{3-6}$cycloalkyl, —$Ar_7$ and -$Het_7$;

$X_1$ is selected from —$C_{1-6}$alkyl-, —O—$C_{1-6}$alkyl, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, —phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is pyrrolidine or piperidine; and $Z_1$, $Z_2$, $Z_3$, $Z_4$ and $Z_5$ are each C.

\* \* \* \* \*

UNITED STATES PATENT AND TRADEMARK OFFICE
CERTIFICATE OF CORRECTION

Page 1 of 2

PATENT NO. : 10,676,486 B2
APPLICATION NO. : 15/505976
DATED : June 9, 2020
INVENTOR(S) : Jan Hoflack, Petra Blom and Pascal Benderitter It is certified that error appears in the above-identified patent and that said Letters Patent is hereby corrected as shown below:

On the Title Page

In item (71), applicant 1, city, delete "Dijon" and insert --Dijon Cedex--, therefor.

In item (73), Assignee 1, city, delete "Dijon" and insert --Dijon Cedex--, therefor.

In Column 2, cite no. 6, delete "Wiken et al., "Higher Monocyte Expressioin of TLR2 and TLR4, and Enhanced Pro-inflammatory Synergy of TLR2 with NOD2 Stimulation in Sarcoidosis", Journal of Clinical Immunology (2009) 29, pp. 78-89." and insert --Wiken et al., "Higher Monocyte Expression of TLR2 and TLR4, and Enhanced Pro-inflammatory Synergy of TLR2 with NOD2 Stimulation in Sarcoidosis", Journal of Clinical Immunology (2009) 29, pp. 78-89.--, therefor.

In the Specification

In Column 2, Line(s) 60, delete "behget's" and insert --behçet's--, therefor.

In Column 4, Line(s) 58, after "-$OR_{35}$,", insert -- –$NR_{11}R_{12}$,--.

In Column 5, Line(s) 18, before "-halo,", insert -- –H,--.

In Column 9, Line(s) 44, delete "-Het;" and insert -- –Het$_7$;--, therefor.

In Column 14, Line(s) 46, delete "behget's" and insert --behçet's--, therefor.

In Column 15, Line(s) 30, delete "-$NR_8$-$SO_2$-$R_4$;" and insert -- –$NR_9$-$SO_2$-$R_4$;--, therefor.

In Column 24, Line(s) 37, before "-$NR_6$-$SO_2$-$R_8$,", insert -- –CN,--.

In Column 26, Line(s) 15, delete "-$NR_{13}R_{20}$;" and insert -- –$NR_{19}R_{20}$;--, therefor.

Signed and Sealed this
Eighth Day of September, 2020

Andrei Iancu
*Director of the United States Patent and Trademark Office*

CERTIFICATE OF CORRECTION (continued)
U.S. Pat. No. 10,676,486 B2

In Column 30, Line(s) 15, after ""*-$C_{1-6}$alkyl-,"", insert -- *-**O-$C_{1-6}$alkyl-, *-S-$C_{1-6}$alkyl-**,--.

In Column 30, Line(s) 36, delete "-Het;" and insert -- –Het$_5$;--, therefor.

In Column 34, Line(s) 64, after "-OH,", insert -- –$C_{1-6}$alkyl,--.

In Column 36, Line(s) 33, delete "-NR$_{13}$R$_{20}$;" and insert -- –NR$_{19}$R$_{20}$;--, therefor.

In Column 37, Line(s) 22, after "-OH,", insert -- –$C_{1-6}$alkyl, -O-$C_{1-6}$alkyl, -S-$C_{1-6}$alkyl,--.

In Column 39, Line(s) 26, before "-halo,", insert -- –H,--.

In Column 39, Line(s) 38, after "-$C_{1-6}$alkyl-,", insert -- –O-$C_{1-6}$alkyl-, -S-$C_{1-6}$alkyl-,--.

In Column 44, Line(s) 65, delete "behget's" and insert --behçet's--, therefor.

In Column 45, Line(s) 21, delete "behget's" and insert --behçet's--, therefor.

In Column 54, Line(s) 33, before "then at", delete "rt" and insert --RT--, therefor.

In Column 55, Line(s) 23, delete "rt." and insert --RT.--, therefor.

In Column 56, Line(s) 66, before "(solution),", delete "rt" and insert --RT--, therefor.

In Column 56, Line(s) 67, delete "16ul" and insert --16ml--, therefor.

In Column 57, Line(s) 1, delete "rt." and insert --RT.--, therefor.